(12) United States Patent
Sanger

(10) Patent No.: US 8,079,704 B2
(45) Date of Patent: Dec. 20, 2011

(54) MULTIFOCAL OPHTHALMIC LENS

(75) Inventor: Demas Sanger, Fukaya (JP)

(73) Assignee: Hoya Corporation, Tokyo (JP)

( * ) Notice: Subject to any disclaimer, the term of this patent is extended or adjusted under 35 U.S.C. 154(b) by 177 days.

(21) Appl. No.: 12/521,563

(22) PCT Filed: Dec. 27, 2007

(86) PCT No.: PCT/JP2007/075084
§ 371 (c)(1),
(2), (4) Date: Jul. 24, 2009

(87) PCT Pub. No.: WO2008/078804
PCT Pub. Date: Jul. 3, 2008

(65) Prior Publication Data
US 2010/0321632 A1 Dec. 23, 2010

(30) Foreign Application Priority Data

Dec. 27, 2006 (JP) ................. 2006-353375

(51) Int. Cl.
*G02C 7/06* (2006.01)
*A61F 2/16* (2006.01)
(52) U.S. Cl. ........ 351/168; 351/161; 351/163; 623/6.28
(58) Field of Classification Search ................. 351/161, 351/168–171; 623/6.11, 6.24, 6.27, 6.28
See application file for complete search history.

(56) References Cited

U.S. PATENT DOCUMENTS

| | | | |
|---|---|---|---|
| 4,752,123 A | 6/1988 | Blaker | |
| 4,813,955 A | 3/1989 | Achatz et al. | |
| 5,139,519 A | 8/1992 | Kalb | |
| 5,517,260 A * | 5/1996 | Glady et al. | 351/169 |
| 2002/0016630 A1* | 2/2002 | Lang | 623/6.28 |
| 2008/0084534 A1 | 4/2008 | Lindacher et al. | |

FOREIGN PATENT DOCUMENTS

| | | |
|---|---|---|
| DE | 3332313 A1 | 4/1985 |
| JP | 62-121419 | 6/1987 |
| JP | 2993022 | 10/1999 |
| JP | 2000-122007 | 4/2000 |
| JP | 2002-536685 | 10/2002 |
| JP | 2006-139292 | 6/2006 |

OTHER PUBLICATIONS

Boettner et al., *Transmission of the Ocular Media*, Investigative Ophthalmology vol. 1, No. 6, pp. 776-783 (Dec. 1962).
PCT International Search Report dated Feb. 5, 2008 for PCT App. Ser. No. PCT/JP2007/075084.

* cited by examiner

*Primary Examiner* — Darryl J Collins
(74) *Attorney, Agent, or Firm* — Henricks, Slavin & Holmes LLP

(57) ABSTRACT

A multifocal ophthalmic lens, including: a far zone for correcting a far vision; and a near zone for correcting a near vision, arranged concentrically in an optical region of the lens, wherein a power distribution is set to vary progressively in radial direction of the far zone and the near zone; power is altered discontinuously to have a stepwise power difference at a boundary between the far zone and the near zone, the value of the power difference at the boundary between the far zone and the near zone is not greater than a maximum value of an intermediate power for correcting an intermediate vision.

45 Claims, 22 Drawing Sheets

MULTIFOCAL OPHTHALMIC LENS

TECHNICAL FIELD

The present invention relates to a multifocal ophthalmic lens, particularly to a multifocal intraocular lens as one example, improved in correcting visual acuity of presbyopic eye.

DESCRIPTION OF RELATED ART

The multifocal ophthalmic lens has a depth of focus deeper than the monofocal ophthalmic lens. This characteristic of the multifocal ophthalmic lens is useful for correcting a presbyopic eye. Generally, a presbyopic eye with a monofocal intraocular lens can clearly see only an image of an object at a far distance and an object located between far distance and intermediate distance, or only an image of an object at a near distance and an object located between near distance and intermediate distance. For example, an eye with a monofocal intraocular lens having refractive power for correcting far vision in which refractive error is about 0 diopter (D), cannot clearly see an object at near distance. Therefore, in this case, an eyeglass is separately required. Hereinafter, diopter is expressed by symbol D in this specification.

Meanwhile, because of the optical design of the lens, a presbyopic eye with a multifocal intraocular lens can clearly see objects at far, near, and intermediate distances. A distance range of near, intermediate, and far visions are from near point of eye to 60 cm, 60 cm to 1.5 m, and 1.5 m to infinity in front of eye, respectively. Although there is no particular definition for distance range of intermediate vision, in the field of ophthalmological optics, a range from 60 cm to 1.5 m in front of eye is regarded as the visual distance of the intermediate vision.

A number of patents describe different concepts for optical design of the multifocal intraocular lens regarding correction of the presbyopic eye. The below are the examples of the inventions related to the optical design of a multifocal intraocular lens applied to the multifocal intraocular lens including a center zone for correcting far vision and an annular zone surrounding the center zone for correcting near vision.

Patent documents 1 and 2 describe the multifocal intraocular lens having a center zone for correcting far vision and an annular zone surrounding the center zone for correcting near vision. When seeing an object at far distance in a bright environment, pupil of eye contracts. In this lighting condition, almost all light is refracted on retina through the center zone (zone for correcting far vision) of the multifocal intraocular lens, therefore, an object at far distance can be clearly seen by a human visual system (eye, retina, optic nerve, brain). In addition, in an average lighting for room or lighting for reading, pupil dilates when seeing an object at near or intermediate distance. Here, the quantity of light refracted on retina by the annular zone (zone for correcting near vision) of the multifocal intraocular lens increases. As a result, objects at near or intermediate distances can be clearly seen.

Optical performance of the multifocal intraocular lens described in the patent documents 1 and 2, is easily affected by the size of a pupil diameter. For example, when an aphakic patient after implanted of intraocular lens to replace the crystalline lens goes out at night, under a lighting condition with extremely low quantity of light, his pupil dilates to near maximum diameter. As the annular zone (region for correcting near vision) is not covered by the pupil iris, ratio of the annular zone area to center zone (zone for correcting far vision) area becomes considerably larger. Accordingly, the quantity of light coming from the center zone that is used for night vision becomes insufficient, resulting almost impossible for a patient to see an object at far distance without eyeglasses.

In view of the circumstance described above, the patent documents 1 and 2 describe the multifocal intraocular lens capable of reducing the dependency of the optical performance to the pupil diameter, by a configuration of repetitive arrangement having the center zone for correcting far vision and the annular zones for correcting near vision. A total area of zones for correcting far vision and a total area of zones for correcting near vision in this intraocular lens are relatively equal. With a lens configuration having these equal areas, a balance between image qualities of far and near vision is retained.

In addition, patent documents 3 and 4 describe a multifocal contact lens having a three-zone optical design. The optics body of this contact lens includes a center zone for correcting far vision, a first annular zone surrounding the center zone for correcting near vision, and a second annular zone surrounding the first annular zone for correcting far vision. Pupil diameter in dim or dark environment is larger than in average lighting condition, here the function of the second annular zone is to surround the light for far vision. In this optical design for a multifocal contact lens, areas of zones for correcting far vision and zones for correcting near vision are designed by taking into account the relation between visual distance and lighting condition with the size variation of pupil diameter.

Further, patent documents 5 and 6 describe the multifocal intraocular lens applying three-zone optical design by taking into account the relation between visual distance and lighting condition with the size variation of pupil diameter having; the center zone (zone for correcting far vision), the first annular zone (zone for correcting near vision), and the second annular zone (zone for correcting far vision). The range of each zone is specified and limited, and lens body of the multifocal intraocular lens is thereby designed.

Patent document 1: German Patent No.3332313A1
Patent document 2: U.S. Pat. No. 4,813,955
Patent document 3: U.S. Pat. No. 4,752,123
Patent document 4: Japanese Patent Laid Open Publication No.62-121419
Patent document 5: U.S. Pat. No. 5,139,519
Patent document 6: Japanese Registered Patent No.2993022

DISCLOSURE OF THE INVENTION

Problem to be Solved by the Invention

In the multifocal intraocular lens having three-zone optical design described in the patent documents 3 to 6 of the aforementioned patent documents, the addition power and its power distribution affect the optical performance more than the areas or diameter ranges in radial direction of the center zone (zone for correcting far vision), the first annular zone (zone for correcting near vision), and the second annular zone (zone for correcting far vision).

For example, as shown in FIG. 11 and FIG. 12, in the multifocal intraocular lens described in the patent documents 5 and 6, a first far zone 103 (center zone) for correcting far vision is arranged in a center zone of an optical zone of an intraocular lens 100. Also, an annular near zone 104 (the first annular zone) is arranged concentrically outside of the first far zone 103. Further, an annular second far zone 105 (the second annular zone) is arranged concentrically outside of the near zone 104. Then, power having relative constant value is set on the near zone 104 (the first annular zone), in a range of 3 to 4 D (2.25 to 3 D in spectacle plane), which is the addition power value prescribed for a patient as a proper power for correcting near vision of the patient. A desired addition power for correcting near vision herein indicates the power prescribed for the patient as the proper power for correcting near vision of the patient. FIG. 12 illustrates a state in which the power of constant value 3.5 D is set in an entire region of the near zone 104 in radial direction of the lens, and a base power, which is a refractive power of an ophthalmic lens required to emmetropize the eye of aphakic patient or presbyopic eye, is set in an entire region of the first far zone 103 (the center zone) and the second far zone 105 (the second annular zone) in radial direction.

However, such distribution of addition power having a relative constant value in the near zone 104 of the multifocal intraocular lens 100 described in the patent documents 5 and 6, provides a shallow depth of focus of near vision. This is because the near zone 104 having the addition power of a constant value has only one focal length for the near vision. The shallow depth of focus of near vision only provides an appropriate image quality of near distance object placed in a narrow range of near distance (for example, 25 to 40 cm in front of eye).

In daily activities, except for a close work distance that requires near vision such as reading, when an eye see objects at near distances, an eye does not see or focus at only one fixed point at near distance, but an eye will continuously see many objects at different near distances from the eye. Shallow depth of focus of near vision causes a difficulty when the eye changes its visual point at near distance from one point to another where their distances from the eye are significantly different, as in the case of comparing foods on table or glancing at headlines and photographs on a newspaper. Meanwhile, when the depth of focus of near vision is deep, the aforementioned difficulty of the near vision is solved, and a useful near vision acuity and a comfortable near vision can be obtained.

Incidentally, in a cataract surgery implanting monofocal intraocular lens, most surgeons will target a post-operative refractive error between −0.5 to −1.0 D (myopia) to compromise the uncorrected far vision with near vision. On the contrary, most of the surgeons practicing multifocal intraocular lens implantation, will target post-operative refractive error of emmetropia or a slight hyperopia (0 to +0.5 D) to completely achieve near vision and uncorrected far vision of the patient. In recent years, cataract surgery has achieved a precision of the post-operative refractive error within about ±0.5 D of the intended refractive error target.

Thus, in a cataract surgery with multifocal intraocular lens, the surgery is performed to achieve emmetropia or slight hyperopia. However, some post-operative refractive error exists in patients implanted with the multifocal intraocular lenses, and some patients are affected with myopia as a result of about ±0.5 D error from the intended post-operative refractive error. In such a patient, even with slight myopia, the uncorrected far vision may deteriorate and halo symptom in which light is diffused around a light source, or glare symptom may appear in a dark environment. Further, in myopia, a near point is shifted closer to the eye of the patient, therefore a near distance interval of the near vision is closer to the eye than the patient expects, and harms the comfort of near vision.

Particularly in the multifocal intraocular lens of the patent documents 3 to 6 of the aforementioned patent documents, the optical performance of the multifocal ophthalmic lens having three-zone optical design is affected by the power distribution characteristics in a boundary region of two adjacent zones for correcting visual acuity. In a case of power discontinuity at the boundary of the center zone (a zone for correcting far vision) and the first annular zone (a zone for correcting near vision) with significant power difference value of power distribution tends to strengthen the bifocal property and weaken the multifocal property of the lens. The ophthalmic lens having bifocal feature can give a high visual acuity and an excellent image quality of far vision and near vision, however give a low visual acuity and a poor image quality of the intermediate vision. Further, power discontinuity of the power distribution with significant power difference value may cause an unwanted image jump phenomenon when a visual point is changed from far vision to near vision and vice versa.

Meanwhile, adding the intermediate zones (transitional zones) having intermediate powers for correcting the intermediate vision at the positions between the center zone and the first annular zone and between the first annular zone and the second annular zone to a multifocal ophthalmic lens, will improve the visual acuity and the image quality of intermediate vision. Certainly, simultaneous images constructed by the intermediate powers in intermediate zone will occasionally superimpose the far and near images on the retina and reduce the image qualities of far and near images.

In addition, actually, in daily activities, intermediate vision corrected by the intermediate zone does not need a high visual acuity level as far vision and near vision needs.

A multifocal ophthalmic lens having wide intermediate zone area deteriorates the image qualities of far vision and near vision. This is because most part of light energy is used by the intermediate zone, the distribution of light energy for zone for correcting far vision and zone for correcting near vision decreases.

Therefore, in view of the circumstances described above, the objective of this present invention is to provide a multifocal ophthalmic lens capable of extending the clearly seen visual ranges of far and near visions and improving the comfort of far and near visions. Further objectives of this invention are to provide a multifocal ophthalmic lens capable of reducing the possibilities of halo and glare symptoms, and minimize the possibility of image jump phenomenon.

SUMMARY OF THE INVENTION

To solve the problems described above, a first aspect of the present invention provides a multifocal ophthalmic lens, including:

a far zone for correcting a far vision; and a near zone for correcting a near vision, arranged concentrically in an optical region of the lens, wherein a power distribution is set to vary progressively in a radial direction of the far zone and the near zone;

power is altered discontinuously to have a stepwise power difference at boundary between the far zone and the near zone; and further a value of the power difference at the boundary between the far zone and the near zone is not greater than a maximum value of an intermediate power for correcting an intermediate vision.

A second aspect of the present invention provides the multifocal ophthalmic lens of the first aspect, wherein a mean power value in the near zone is less than an addition power prescribed for a patient, as a proper power for correcting near vision of the patient.

A third aspect of the present invention provides the multifocal ophthalmic lens of the first or second aspect, wherein a region having a mean power value that is negative relative to the reference power is included in the far zone.

A fourth aspect of the present invention provides the multifocal ophthalmic lens in any of the first to third aspects, wherein region of the far zone next to the near zone has the mean power value that is positive relative to the reference power.

A fifth aspect of the present invention provides the multifocal ophthalmic lens in any of the first to fourth aspects, wherein a first far zone is arranged in a center zone of the optical region, and an annular near zone is arranged concentrically outside the region of the first far zone, and an annular second far zone is arranged concentrically outside the annular near zone.

A sixth aspect of the present invention provides the multifocal ophthalmic lens of the fifth aspect, wherein the addition power value of a region of the near zone next to the second far zone is less than an addition power value of a region of the near zone next to the first far zone.

A seventh aspect of the present invention provides the multifocal ophthalmic lens of the fifth or sixth aspect, wherein the power value of a region of the second far zone next to the near zone is less than the power value of a region of the first far zone next to the near zone.

An eighth aspect of the present invention provides the multifocal ophthalmic lens in any of the fifth to seventh aspects, wherein the power value of an outer region of the second far zone is less than the power value of a region of the second far zone next to the near zone.

A ninth aspect of the present invention provides the multifocal ophthalmic lens in any of the fifth to eighth aspects, wherein the mean power value of the outer region of the second far zone is negative relative to the reference power.

A tenth aspect of the present invention provides the multifocal ophthalmic lens in any of the first to fourth aspects, wherein the near zone is arranged in a center zone of the optical region, and an annular far zone is arranged concentrically outside the region of the near zone.

An eleventh aspect of the present invention provides the multifocal ophthalmic lens of the tenth aspect, wherein the power value of the outer region of the far zone is less than the power value of the region of the far zone next to the near zone.

A twelfth aspect of the present invention provides the multifocal ophthalmic lens of the tenth or eleventh aspect, wherein the mean power value of the outer region of the far zone is negative relative to the reference power.

A thirteenth aspect of the present invention provides a multifocal ophthalmic lens, including:
  at least one far zone for correcting a far vision;
  at least one near zone for correcting a near vision,
  arranged concentrically in an optical region of the lens,
  wherein a power distribution is set to vary progressively in radial direction of the far zone and the near zone;
  power is altered discontinuously to have a stepwise power difference at a boundary between the far zone and the near zone;
  a progressive power distribution of the near zone in the vicinity of the boundary between the far zone and the near zone has a value close to a maximum value of an intermediate power for correcting an intermediate vision at the boundary;
  the progressive power distribution of the near zone is designed to have a mountain-shaped power distribution, and the maximum value at a peak of this mountain-shaped power distribution is set to a power required for correcting visual acuity for seeing an object at the intended nearest distance or at a reading distance;

the progressive power distribution of the near zone is a distribution in which power gradually increases from the boundary between the near zone an the far zone to the peak of the mountain-shaped power distribution; and
  the mean power value of the far zone is less than a reference power.

A fourteenth aspect of the present invention provides the multifocal ophthalmic lens, wherein the ophthalmic lens includes an UV-absorber and/or a blue light blocking dye.

A fifteenth aspect of the present invention provides the multifocal ophthalmic lens, wherein the ophthalmic lens in any of the first to fourteenth aspects is an intraocular lens to be implanted inside an eye.

ADVANTAGE OF THE INVENTION

According to the present invention, a power distribution is set to vary progressively in an entire region of a far zone and a near zone in radial direction. Therefore, the depth of focus of far vision provided by the far zone and the depth of focus of near vision provided by the near zone can be deepened. As a result, clearly seen ranges of the far vision and near vision can be extended, therefore comfort of far vision and near vision can be improved.

In addition, according to the present invention, the possibilities of halo and glare symptoms can be reduced, and the possibility of image jump can be minimized.

BEST MODE FOR CARRYING OUT THE INVENTION

[A] First Embodiment (FIG. 1 to FIG. 9)

FIG. 1 is a front view illustration of an intraocular lens, being a first embodiment of an ophthalmic lens according to the present invention, and FIG. 2 is an illustration of a lens body 11 of the intraocular lens, being the first embodiment of the ophthalmic lens according to the present invention, wherein FIG. 2(A) is a side view of the lens body 11 of the intraocular lens shown in FIG. 1, and FIG. 2(B) is a front view of the lens body 11 of the intraocular lens in FIG. 1. FIG. 3 is a graph showing a power distribution in radial direction of the lens of the lens body 11 of the intraocular lens shown in FIG. 1 and FIG. 2. FIG. 4 is an illustration of a comparison of a depth of focus of the intraocular lens according to the first embodiment shown in FIG. 1 and FIG. 2, and the depth of focus of the intraocular lens according to the conventional art, wherein FIG. 4(A) illustrates a case of the intraocular lens according to the conventional art and FIG. 4(B) illustrates a case of the intraocular lens according to the first embodiment. FIG. 5 is an illustration of a comparison of a far point and a near point of the intraocular lens according to the first embodiment shown in FIG. 1 and FIG. 2, and a far point and a near point of the intraocular lens according to the conventional art, wherein FIG. 5(A) illustrates a case of the intraocular lens of the conventional art, and FIG. 5(B) illustrates a case of the intraocular lens according to the first embodiment. FIG. 6 is an illustration of a comparison of halo symptom of the intraocular lens according to the first embodiment, and halo symptom of the intraocular lens according to the conventional art, wherein FIG. 6(A) illustrates a case of the intraocular lens of the conventional art, and FIG. 6(B) illustrates a case of the intraocular lens according to the first embodiment. Preferred embodiments of the present invention will be described hereunder, by referring to the drawings.

An intraocular lens 10 shown in FIG. 1 and FIG. 2 is a multifocal ophthalmic lens for correcting visual acuity such as a presbyopic eye, including a lens body 11 and a support member 12.

An optical region of the lens body 11 has three zones for correcting visual acuity; a first far zone 13 arranged in a center zone of the optical region of the lens, an annular near zone 14 arranged concentrically outside the outer region of the first far zone 13, and an annular second far zone 15 arranged concentrically outside the outer region of the near zone 14, respectively.

A plurality of support member 12 shown in FIG. 1 protrude from the lens body 11, are made of the same or different material from the material of the lens body 11. Each support member 12 is provided for positioning the optical region of the lens body 11 at the intended position inside or outside of an eye of a lens wearer. Note that the support member 12 is a flange zone formed around the optical region of the lens when the ophthalmic lens is a contact lens, and is an eyeglass frame when the ophthalmic lens is an eyeglass lens.

The lens body 11 is described in detail herein. A first far zone 13 and a second far zone 15 in the lens body 11 are zones for correcting far vision, and a near zone 14 is a region for correcting near vision. As shown in FIG. 3, the power distribution is set to vary progressively in each entire region of the first far zone 13, the near zone 14, and the second distance zone 15, in radial direction. Moreover, power is set to be altered discontinuously to have a stepwise power difference at the boundary between the first far zone 13 and the near zone 14 and at the boundary between the near zone 14 and the second far zone 15. At this boundary where the power alters abruptly, the power distribution jumps from a minimum intermediate power in the far zone, to a maximum intermediate power in the near zone. The minimum intermediate power is a refractive power of a lens required for seeing an object located at a maximum intermediate distance (for example, 1.5 m). The maximum intermediate power is a refractive power of a lens required for seeing an object located at a minimum intermediate distance (for example 60 cm). In addition, here, an intermediate distance refers to a distance between a far distance and a near distance, and the minimum intermediate distance refers to a nearest distance of the intermediate distance, and the maximum intermediate distance refers to a farthest distance of the intermediate distance. Further, an intermediate power refers to a mid power between a far power and a near power, and the minimum intermediate power refers to a lowest power of the intermediate powers, and the maximum intermediate power refers to a greatest power of the intermediate powers.

Further, in FIG. 3, an inner sub-region A of the lens in the first far zone 13 is set to have a mean power value equal to or less than and negative relative to the reference power. In addition, here, the reference power refers to a refractive power of ophthalmic lens required to emmetropize the eye of aphakic patient or presbyopic eye, and is otherwise called a base power. The term reference power is used in the above definition, hereunder. In addition, the power of an outer sub-region B of the lens in the first far zone 13, namely a region B next to the near zone 14 in the first far zone 13 is set to have a mean power value greater than and positive relative to the reference power (base power). The power distribution of the sub-region B has a value about the reference power (base power) at the radius distance a1, and gradually increases to about the minimum intermediate power at radius distance a. Further, in the second far zone 15, the power of an inner sub-region C of the lens, namely the sub-region C next to the near zone 14 is set to have a mean power value greater than and positive relative to the reference power. The power distribution of the sub-region C has a value about the minimum intermediate power at radius distance b, and is gradually decreases to about the reference power at the radius distance b1. Moreover, an outer sub-region D of the lens in the second far zone 15 is set to have a mean power value equal to or less than and negative relative to the reference power. The power value at radius distance b1 in the sub-region D is about the reference power. The power distribution of the sub-region D has a relatively constant power with increase of radius distance (from the radius distance b1 to the radius distance c), or gradually decreases as the radius distance increases. Further, the mean power of the near zone 14 is set to a value less than the desired addition power (3 to 4 D; about 2.25 to 3 D in spectacle plane). The desired addition power herein is the mean power of the sub-region in the vicinity of point p, and is the addition power prescribed for a patient as a proper power for correcting near vision of the patient. This addition power is a power value required for reading at distance of 30 to 40 cm and differs on each patient. Generally, this power is 3 to 4 D. When the power prescribed for a patient as a proper power for correcting near vision of the patient is about 3.5 D, the mean power of the sub-region in the vicinity of point p is about 3.5 D.

Incidentally, to design the power distribution mentioned above, the refractive power and spherical aberration of cornea from the center to the peripheral of cornea need to be considered.

FIG. 18 illustrates the characteristics of the corneal spherical aberration. In FIG. 18, paraxial rays at radial height of cornea hn (n=0, 1, 2, 3 . . . , h0 is the radial height of paraxial ray from the cornea center) above the visual axis are refracted each to a point in front of focal point f0 inside the eye. The greater radial height of cornea hn, the greater point Pn shifts from focal f0 to cornea side. The greater radial height of paraxial ray from the cornea center, the greater this paraxial ray will be refracted. In other words, the refractive power and spherical aberration of cornea increase with the increase of height from the cornea center.

Therefore, since the corneal refractive power and the corneal spherical aberration have the characteristics as described above, in order to optimize the optical performances of the multifocal ophthalmic lens, the corneal spherical aberration needs to be considered in designing a multifocal ophthalmic lens.

How the corneal spherical aberration is taken into account, is described below in detail by referring to an intraocular lens.

FIG. 19 illustrates a state in which light rays are emitted from a light source located at distance of 60 cm in front of a cornea model.

Ray Lx coming to cornea at radial height x1 above the cornea center is refracted by cornea at position x2 to point Px.

Ray Ly coming to cornea at radial height x2 above the cornea center is refracted by cornea at position y2 to point Py.

As described above, since radius y2 is greater than radius x2, the refractive power at y2 is greater than the refractive power at x2. Therefore, ray Ly is refracted to point Py which is nearer to cornea than point Px.

As a result, to clearly see an object, point Px and point Py need to be coincidently positioned on the retina. Namely, to position coincidently the point Px and point Py on the retina, from the condition shown in FIG. 19, a refractive power to be added to refract ray Lx at position x2 of cornea needs to be greater than a refractive power to be added to refract Ly at position y2 of cornea.

As described above, in this embodiment, the position of the retina is the focal plane of the optical system of the cornea and the lens. FIG. 20 illustrates light rays refracted by the cornea and the lens, are focused coincidently to the retina. As shown in FIG. 20, to refract ray Lx and ray Ly to the retina, an intraocular lens needs greater refractive power to be added at radial height a for ray Lx than the refractive power to be added at radial height b for ray Ly. To refract ray Lx and ray Ly to the retina, a lens is placed behind the cornea as shown in FIG. 22. This is because to refract ray Lx and ray Ly to the retina, the refractive power at radial height a must be greater than the refractive power at radial height b.

The addition power of values α at radial height a and β at radial height b are used to refract the light rays from a distance of 60 cm (the nearest intermediate distance) in front of the cornea to the retina. Here, α is the maximum value of intermediate power at radial height a, and β is the maximum value of intermediate power at radial height b in the near zone 14.

FIG. 21 illustrates the light rays from a distance of 1.5 m in front of a cornea model. As illustrated in FIG. 19, ray Lx coming to cornea at radial height x1 above the cornea center is refracted by cornea at position x2 to point Px.

Ray Ly coming to cornea at radial height y2 above the cornea center is refracted by cornea at position y2 to point Py.

Ray Ly is refracted to the retina with a refractive power δ at radial height b.

To refract ray Lx and ray Ly to the retina, the refractive power at radial height a must be greater than the refractive power at radial height b.

To refract ray Lx on the retina the refractive power γ at radial height a must be greater than the refractive power δ.

The addition power of values γ at radial height a and δ at radial height b are used to refract the light rays on from a distance of 1.5 m (the farthest intermediate distance) in front of the cornea. Here, γ is the minimum value of intermediate power at radial height a in the first far zone 13, and δ is the minimum value of intermediate power at radial height b in the second far zone 15.

By considering the refractive power of cornea is greater at radius a than at radius b, the addition power of lens or power value at radius a is preferably made greater than at radius b.

Further, addition power of value a of the near zone 14 at radial height a is preferably greater than the addition power value β of the near zone 14 at radial height b.

Furthermore, the power value y of the first far zone 13 at radial height a is preferably greater than the power value δ of the second far zone 15 at radial height b.

The optical structure of the aforementioned first far zone 13, near zone 14, and second far zone 15 are explained further in detail.

In the intraocular lens 10 herein, the power distributions of the first far zone 13, the near zone 14, and the second far zone 15 are made on the anterior surface 16 of the intraocular lens 10, however the power distributions of the aforementioned first far zone 13, near zone 14, and second far zone 15 can also be made on the posterior surface 17.

(1) Near Zone 14

The near zone 14 has a power distribution that is progressively altered from power value α to power value β at points where power alters abruptly (hereinafter referred to as inflection point), in an entire region (range from point a to point b in FIG. 2 and FIG. 3) in radial direction. In the aforementioned power distribution, an upward convex curve is preferably made, wherein the addition power of the lens is maximized at point p. With the power distribution having an upward convex curve, an ophthalmic lens can be made having gradual progressive configuration. The mean power of the sub-region in the vicinity of point p is about the value of a desired addition power. A desired addition power herein, means the addition power prescribed for a patient, as a proper power for correcting near vision of a patient. The term "the desired addition power" is used in the above definition hereunder. The desired addition power is a power required for seeing an object at reading distance of 30 to 40 cm, and differs on each patient. Generally, this power is 3 to 4 D. When the power prescribed for a patient as a proper power for correcting near vision of the patient is about 3.5 D, the mean power of the sub-region in the vicinity of point p is about 3.5 D.

The aforementioned power distribution is specifically described herein. The power distribution of the progressive part of the region in the near zone 14 in FIG. 3, has powers changed smoothly in the vicinity of the peak p of the convex-shaped curve, to make the visual acuity of near vision acuity close to the maximum visual acuity even when the pupil diameter changes. However, the power distribution of the progressive part of the region in the near zone 14 alters rapidly when moving close to α and β. The change in the power distribution curve of the progressive part of this near zone 14 is explained herein with the gradient of the tangent and the radius of the lens. The gradient of the power distribution curve in the region of the near zone 14 changes from a positive gradient value at radius a to gradient value of zero at radius p, and to negative gradient value at radius b. Namely, the absolute value of the gradient of the power distribution curve in progressive part of the near zone 14 decreases when the radius from center O increases from radius a to radius p, and the absolute value of the gradient of the power distribution curve in progressive part of the near zone 14 increases when the radius from center O increases from radius p to radius b. The designed power value of power distribution in the first far zone 13, the near zone 14, or the second far zone 15 can be expressed by the following polynomial equation (Equation 1).

$$P_m(r) = a_n r^n + a_{n-1} r^{n-1} + a_{n-2} r^{n-2} + \ldots + a_2 r^2 + a_1 r^1 + a_0$$

where
P: Refractive power at radius r
r: Radius or distance from lens center
m: Index of lens zone
a: Constant
n: Order of polynomial equation Power variation in the progressive parts of the first far zone 13, the near zone 14, and the second far zone 15 in FIG. 3, when computing the aforementioned polynomial equation with the fourth order, can be expressed by the following equations. In the example of this embodiment of multifocal intraocular lens having power +21 D described in below with reference to FIG. 3 and FIG. 22, the power of the progressive part of the near zone 14 is expressed by polynomial P14($r$), the power of the progressive part of the far zone 13 in the center zone of lens is expressed by polynomial P13($r$), and the progressive part of the second far zone 15, that is the far annular zone in the peripheral of lens is expressed by polynomial P15($r$) (Equations 2-4).

$$P_{13}(r) = 5.579271 r^4 - 6.404604 r^3 + 1.352660 r^2 - 0.172927 r^1 + 21.000059$$

$$P_{14}(r) = 30.841108 r^4 - 164.546812 r^3 + 312.553124 r^2 - 247.902804 r^1 + 91.932185$$

$$P_{15}(r) = 0.987169 r^4 - 10.048864 r^3 + 38.048551 r^2 - 64.889717 r^1 + 62.857009$$

The power 3.5 D at point p represents normal reading distance of 35 cm. To obtain a maximum near visual acuity of a wearer, the radial height of point p is set to about 1.5 mm. This value is half of 3.0 mm, the average pupil diameter under typical indoor lighting condition. Further, point p is preferably set to a position slightly closer to the lens center O so that the near vision can be retained even when the average pupil diameter becomes smaller in lighting condition brighter than the aforementioned typical lighting.

The aforementioned power α and power β are the required powers for seeing an object at position 60 cm in front of eye, for example α=2.0 and β=1.6 D. When the maximum addition power is 4.0 D, the maximum near visual distance is about 30 cm. In this case, as the near zone 14 has all power values for focusing light coming from the intended range of near distances, such as range Wi (FIG. 4(B)) from 30 to 60 cm in front of eye, the clearly seen range of the near vision will be extended. Since objects at different near distances can be clearly seen, the comfort of near vision will be improved. As described earlier, with the condition α>β and taking into account the aforementioned spherical aberration, the refracted light rays can be focused on the retina.

Whereas, in the intraocular lens 100 of conventional art shown in FIG. 11 and FIG. 12, the power distribution of the near zone 104 is more affected by the spherical aberration towards the lens peripheral. In the power distribution curve, the power increases in the direction towards the lens peripheral, however, the power changes only within constant range in the first far zone, the near zone, and the second far zone. Thus the depth of focus of near vision is shallow and will provide clear image quality only for reading distance (range Wp (FIG. 4(A) from 25 to 35 cm in front of eye), as an example. In addition, due to the integral effect of the aforementioned lens spherical aberration and the corneal spherical aberration, when the pupil diameter enlarges, the expected visual acuity of far vision decreases in lens of the conventional art. In FIG. 4, FIG. 5, and FIG. 6, numeral 18 indicates the retina.

In the near zone 14 of the intraocular lens 10 of this embodiment shown in FIG. 2 and FIG. 3, the power is set to a value less than the addition power prescribed for a patient as a proper power for correcting the near vision of the patient. Namely, in the conventional art shown in FIG. 11 and FIG. 12, although the addition power of the near zone 104 slightly increases in a range of 3 to 4 D, the addition power is set to almost a constant value. Meanwhile, in the near zone 14 of this embodiment, shown in FIG. 3, the mean power of the near zone 14 is designed to have a value of equal to or less than 3.0 D.

The near point 1 (FIG. 5(A),(B)) is a near point clearly seen by the near vision of an aphakic patient being neither hyperopia nor myopia but emmetropia after intraocular lens implantation that replaced the crystalline lens. A near point of an aphakic patient being myopia after the aforementioned intraocular lens implantation is the near point 2 (FIG. 5(A)(B) in the conventional art, and the near point 3 (FIG. 5(B)) in this embodiment. Since the mean addition power of a conventional art is greater than the mean addition power of this embodiment, distance Li between the near point 3 and the near point 1 is shorter than distance Lp between the near point 2 and the near point 1. As the near point 3 of this embodiment is not excessively close to the eye, the visual performance of near vision can be retained. Further, the far point 2 is closer to the eye than the far point 3, therefore the eye with this embodiment can see an object between the far point 2 and the far point 3.

In the near zone 14 of the intraocular lens 10 of this embodiment, a power range of a power distribution of near vision is greater than the power range of the near zone 104 of the lens 100. In addition, the mean power is set to a value less than the addition power prescribed for a patient as a proper power for correcting the near vision of the patient. Therefore, as shown in FIG. 6(B), a focal length Fi of the near zone 14 lengthens. Namely, the position of focused light is farther apart from the intraocular lens 10. Therefore, light passing through the near zone 14 will be focused on the retina 18, thus reducing the possibilities of halo and glare symptoms in a dark environment. Beside reducing the possibilities of halo and glare symptoms, since the clearly seen near point is not excessively close to the eye, the visual performance of the near vision can be retained. By making the near zone 14 having progressive configuration between radial heights a and p, and between radial heights p and b, and setting the addition power α at radial height a and the addition power β at radial height b, so that α>β, the distance range of near vision where an object can be clearly seen is extended, and the image of object can be clearly seen at the retina.

Meanwhile, in the conventional art, when the mean power of the near zone 104 of the intraocular lens 100 is set to a value greater than the addition power prescribed for a patient as a proper power for correcting the near vision of the patient, the focal length Fp of the near zone 104, is shorter than the focal length Fi, as shown in FIG. 6(A). Therefore, the position of the focused light that passes through the near zone 104 is closer to the intraocular lens 100, and because the light is distributed wider on the retina 18, the possibilities of halo and glare symptoms will increase in the dark environment.

(2) First far zone 13 and second far zone 15

The first far zone 13 shown in FIG. 2 and FIG. 3 is designed to have powers to vary progressively from power that is negative relative to the reference power to positive power γ, in an entire region (range from point 0 to point a in FIG. 3) in radial direction.

Also, the second far zone 15 is designed to have powers vary progressively from power δ that is positive relative to the reference power to negative power in an entire region (range from point b to point c in FIG. 3) in radial direction.

The powers γ and δ herein are the powers required for seeing an object at distance 1.5 m in front of eye. The first far zone 13 and the second far zone 15 will deepen the depth of focus of far vision, widen a clearly seen range Xi (FIG. 4(B)) of the far vision (for example in the range of 1.5 to 6 m), and improve comfort of far vision.

Meanwhile, in the first far zone 103 and the second far zone 105 of the intraocular lens 100 shown in FIG. 11 and FIG. 12, the power distribution values are almost constant and close to the reference power value. Therefore, intraocular lens 100 has shallow depth of focus of far vision, distance range Xp (FIG. 4(A)) of far vision where an object can be clearly seen (for example in the range of 2 to 6 m) is narrower than the range Xi of this embodiment, and lower comfort of far vision.

In the intraocular lens 10 shown in FIG. 2 and FIG. 3, powers of the inner sub-region of the lens in the first far zone 13, and powers of the outer sub-region of the lens in the second far zone 15 are set to have a mean power value equal to or less than and negative relative to the reference power. Thus, the optical power of eye of a wearer of the intraocular lens 10 can be shifted to the hyperopic side, and this slight hyperopia (+0.3 D or less) can improve the image quality of far vision of the wearer of the intraocular lens 10.

The far point 1 (FIG. 5) is the point at far distance where an object can be clearly seen by the far vision of an aphakic patient being neither hyperopia nor myopia but emmetropia after intraocular lens implantation that replaced the crystalline lens. A far point of an aphakic patient being myopia after the implantation of intraocular lens 10 of this embodiment is the far point 3. This is because sub-regions of the first far zone 13 and the second far zone 15 of the intraocular lens 10 having the mean power value that is negative relative to the reference power, cancels the myopic power of the patient by shifting the optical power of this patient to the hyperopic side.

In addition, in comparing the focused image in FIGS. 6(A) and (B), the center image of the conventional art (A) spreads wider than the center image of this embodiment (B), and the center image blurs wider with the increasing radius from the center point. This means that the conventional art in FIG. 6(A) can not obtain a clear far vision in the center image and its peripheral, namely with the first far zone and the second far zone of the intraocular lens. On the contrary, this embodiment in FIG. 6(B), can obtain a clear visual field by setting a mean power value that is negative relative to the reference power in the first far zone and the second far zone and canceling the aforementioned spherical aberration in the cornea.

As a result, a part of an excesive power value that is positive relative to the reference power, can be canceled by the sub-regions having the mean power values that are negative relative to the reference power in the first far zone 13 and the second far zone 15, and myopia can be reduced. Further, the effect of corneal spherical aberration that increases with the increase of the radial height of cornea can be canceled by the sub-region having the mean power value negative that is relative to the reference power of the second far zone 15.

In considering the corneal spherical aberration, here the power value γ at radius a in the first far zone 13 of the lens is preferably greater than the power value δ at radius b in the second far zone 15 of the lens.

In the intraocular lens 100 of the conventional art in FIG. 11 and FIG. 12, the power of the first far zone 103 and the second far zone 105 is set to be the reference power (0 D). Therefore, the optical power of the eye of the wearer of the intraocular lens 100 can not be shifted to slight hyperopic side. The far point 2 (FIG. 5(A)) is the far point of a patient having an aphakic eye being myopia after the implantation of intraocular lens 100. Distance Mi between the far point 3 and the far point 1 is shorter than distance Mp between the far point 2 and the far point 1, and therefore the myopia of the wearer of the intraocular lens 10 of this embodiment is reduced. Thus, the image quality of the far vision of the eye of a lens wearer will be improved, and the possibilities of halo and glare symptoms in the dark environment can be reduced.

(3) Boundary of the first far zone 13, the second far zone 15, and the near zone 14

As shown in FIG. 3, the intraocular lens 10 has a boundary between the first far zone 13 and a near zone 14 (powers γ to α at inflection point), and the boundary between the near zone 14 and the second far zone 15 (powers β to δ at inflection point) having powers altered discontinuously to have a stepwise power difference. Accordingly, the light energy passing through the intraocular lens 10 is used only for the far vision by the first far zone 13 and the second far zone 15, and the near vision by the near zone 14. As a result, an image of far vision and an image of near vision are clearer than those of the intraocular lens having the intermediate zone for intermediate power, and the image quality (contrast and sharpness) of the far vision and the near vision can be improved.

Height of discontinuous power step (power difference) at the boundary between the first far zone 13 and the near zone 14 and the boundary between the near zone 14 and the second far zone 15 has a sufficient power difference for separating the image of far vision from the image of near vision on the retina 18. A human visual system (eye, retina, optic nerve, and brain) selectively sees a clear image of far vision or image of near vision as intended, and does not see both images simultaneously. Namely, in the conventional art, the images constructed by the intermediate zone having intermediate power (intermediate images) superimpose with the image of far vision and with the image of near vision and mix the constructed images. Meanwhile, the lens of this embodiment has a sufficient discontinuous power difference for separating the image of far vision from the image of near vision on the retina, and therefore the appearance of such a mixing of the constructed image can be prevented.

In addition, as shown in FIG. 3, both sub-regions next to the near zones 14 in the first far zone 13 and the second far zone 15 are set to have mean power values greater than and positive relative to the reference power (0 D). Thus, the power difference can be reduced at the boundary between the first far zone 13 and the near zone 14, and at the boundary between the near zone 14 and the second far zone 15; in this embodiment, the power difference is set to a value in a range of 1 to 2 D. As a result, the possibility of an image jump phenomenon is reduced, and when a visual field is changed between seeing an object at far distance and seeing an object at near distance, the comfort of vision when changing the visual field can be obtained.

Since the near zone 14 has a progressive configuration, its mean power value is less than the addition power prescribed for a patient as a proper power for correcting the near vision of the patient. Thus, values α and β are smaller than a desired addition power. Further, by setting the mean power value that is positive relative to the reference power to power γ of the near region in the first far zone 13 and to power δ of the near region in the second far zone 15, the intervals of γ to α and β to δ become small. Thus, image jump, halo and glare symptoms can be minimized.

In addition, in the conventional art as shown in FIG. 12, the power distribution is set so that the power is abruptly altered at the boundary between the zone for correcting far vision and a zone for correcting near vision. Namely, by an abrupt alteration of a curvature at the inflection point (line) where curvature surface of the far zone for far power and curvature surface of the near zone for near power intersect each other, this inflection point (line) may become a source generating glare. Further, machining is difficult to perform in accordance with the aforementioned setting. However, in this embodiment as shown in FIG. 3, by setting the mean power value at the aforementioned boundary, the alteration of its curvature becomes smooth, and the possibility of glare can be reduced. Further, machining will be easier, leading to an improvement of yield.

An example of the present invention will be given hereunder.

In FIG. 3 and FIG. 22, the base power 0 represents the intraocular lens power of 21 D. Here, powers at radius distances a=1.05 mm and b=1.75 mm in the near zone are 22.97 D and 22.64 D, respectively. Also, powers at radius distances a=1.05 mm and b=1.75 mm in the far zone are 21.60 D and 21.28 D, respectively.

Therefore, the difference between the addition power value α at radius distance a in the near zone 14 of the lens, the addition power value β at radius distance b in the near zone 14 of the lens, the addition power value γ at radius distance a in the first far zone 13 of the lens, and addition power value δ at radius distance b in the second far zone 15 of the lens and the base power 0 D are 1.97(=22.97−21.0), 1.64(=22.64−21.0), 0.60(=21.60−21.0), and 0.28(=21.28−21.0)D, respectively.

The value ρ at radius distance p between radius distances a and b, is the greater addition power that is determined on the basis of the nearest distance.

When the values of the nearest distance as the intermediate distance and the radius distance are set to 30 cm and 1.4 mm, respectively, power at radius distance 1.4 mm is 25.13 D, and ρ is 4.13 D.

When the values of the nearest distance as the intermediate distance is set to 35 cm, power at radius distance 1.4 mm is 24.49 D, and ρ is 3.49 D.

The aforementioned power is obtained by computer calculation of the cornea model and the optical system of the lenses shown in Table 1 using the ray tracing method. This type of invented d lens is designed by modeling the optical system of cornea and ray tracing method using a widely sold and known optical design software such as the optical design and evaluation program CODE V (registered trademark), a product of Optical Research Associates, and optical system design software ZEMAX(registered trademark), a product of ZEMAX Development Corporation, USA.

In a lens made of a material having different refractive index or an optical body having different shape, the values of α, β, γ, and δ differ slightly from the aforementioned values. In addition, the values of α, β, γ, and δ also differ slightly from the aforementioned values when the lens is designed with different cornea model. However, knowledge regarding this example and this embodiment can be applied for designing a lens having parameters different from the aforementioned examples, such as refractive index, optical body shape, and parameters.

As a specific example of FIG. 6, FIG. 24 and FIG. 25 show the results of halo simulation by using software ZEMAX, with aperture diameter set to 4 mm and 5 mm, respectively. FIG. 24(A) and FIG. 25(A) are the results of conventional arts, and FIG. 24(B) and FIG. 25(B) are the results of this embodiment. Table 1 show the parameters of an eye model of the conventional art and this embodiment.

In this example, a circular object of a light source having a diameter of 20 cm is located at a distance of 60 m in front of the eye model having parameters shown in Table 1. In a real life, this circular object can be a traffic signal at night, as an example.

Light rays refracted by the near zone of the intraocular lens appear as a halo pattern surrounding the center image of the light source. Here, halo appears larger than the actual image of the light source. Then, halo surrounds the center image constructed by the far zone of the lens. Normally, in comparison with lens having near zone wherein the near zone next to the far zone has lower mean power, the greater mean value of the near zone of the lens, the larger and the denser halo pattern will be.

The mean power in the near zone of the lens in the conventional art, is designed greater than the mean power of the near zone of the lens of this example. Therefore, as shown in FIG. 24 and FIG. 25, the size of halo pattern of lens of the conventional art is larger than the size of halo pattern of lens of this example. Also, as shown in FIG. 25, halo pattern of lens in conventional art becomes denser than halo pattern of lens of this example. Namely, the light intensity of halo pattern of lens of this example is less than that of the halo pattern of lens in the conventional art, and with a lens of this example, a patient will hardly feel inconvenient. Namely, it suggests that a patient implanted with a lens of this example will be less bothered by halo symptoms at night than a patient implanted with a lens of the conventional art.

The performance of a multifocal intraocular lens is affected by the configuration of each region of zones for correcting far vision and zones for correcting near vision in the lens, the addition power, and the power distribution, and so forth. The optical performance of a multifocal intraocular lens can be shown by a distance-visual acuity graph showing the relation between the distance of object and the visual acuity when seeing it, and a distance-contrast graph showing the relation between the distance of object and the contrast (MTF value) that represents the image property. In relation with this, the results given by the graphs of the multifocal intraocular lens of the first embodiment and the multifocal intraocular lens of the conventional art are explained hereunder.

The optical performances are affected by the aperture diameter of the lens and the pupil diameter of an aphakic patient. Results relating with a case where these diameter change are also given. In addition, FIG. 7 shows the configuration of the far zone and the near zone in both the multifocal intraocular lens of the first embodiment and of the conventional art. Further, the base powers of both lenses are 21.0 D, and those power distributions are shown in FIG. 3 and FIG. 12. The maximum addition power of the near zone of the lens is about 3.5 D in both lenses. Also, the near zone of this embodiment has the mean addition power of about 3.5 D in the sub-region in the vicinity of the peak of the power distribution, and other sub-regions of the near zone have the mean addition powers equal to or less than 3.5 D. Meanwhile, the lens of the conventional art has the addition power that almost constant about 3.5 D in all sub-regions of the near zone.

To prepare the aforementioned graphs for the evaluation, image simulation with eye model having parameters shown in Table 1 was performed by using the optical system design software ZEMAX (registered trademark), a product of ZEMAX Development Corporation, USA. The evaluation was made for each aperture diameter (2.5, 3.0, 3.5, and 4.0 mm) that represents the pupil diameter of an aphakic patient. The visual acuities that still can be recognized on the images of the simulated visual acuity charts were evaluated on 10 observers. The mean value of the highest visual acuities that can be recognized at each distance was set as the visual acuity, and the distance-visual acuity graph (FIG. 8) was drawn for each aperture diameter, in which the horizontal axis and vertical axis are distance and virtual acuity, respectively.

TABLE 1

Eye model parameters

| | Curvature radius (mm) | Conic constant Note 2) | Thickness (mm) | Refractive index |
|---|---|---|---|---|
| Anterior surface of cornea | 7.8 | −0.23 | 0.55 | 1.3771 |
| Posterior surface of cornea | 6.5 | 0 | 4.07 | 1.336 |
| Aperture | — | — | 0 | 1.336 |
| Anterior surface of intraocular lens | Note 1) | 0 | 0.78 | 1.517 |
| Posterior surface of intraocular lens | −30.00 | 0 | 18.38 | 1.336 |
| Retina | — | — | — | — |

Note 1)
The curvature radius of the anterior surface of intraocular lenses is on the multifocal surfaces of the intraocular lenses of this embodiment and conventional art, the curvature radius at the center of the multifocal surface was set to 12.06 mm.

Note 2)
To reduce the corneal aberration, a conic constant in the anterior surface of the cornea was used in the simulation with ZEMAX.

Further, to evaluate the distance-visual acuity graph, Landolt ring visual acuity chart (see FIG. 13) showing visual acuity index 0.2 (Landolt ring) to visual acuity index 1.0 and eye model shown in Table 1 were used to simulate the visual acuity chart images constructed by the intraocular lens 10 of this embodiment and the intraocular lens 100 of the conventional art for each aperture diameter with Zemax. The result samples of the image simulation results of this embodiment and the conventional art for each distance are shown in FIG. 14 to FIG. 17.

Visual acuity of 0.3 or greater is required for clearly seeing an object up to 60 cm in front of eye (near vision). FIG. 8(a) (b) (c) (d) and Table 2 show the comparison between the range Wi clearly seen by an eye with the intraocular lens 10 of this embodiment having near vision visual acuity 0.3 or greater and the range Wp clearly seen by an eye with the intraocular lens 100 of the conventional art having near vision visual acuity 0.3 or greater for each aperture diameter (2.5, 3.0, 3.5, and 4.0 mm).

TABLE 2

| Aperture diameter (mm) | Embodiment example Distance range Wi | Conventional art Distance range Wp |
| --- | --- | --- |
| 2.5 | 40~60 | 29~42 |
| 3.0 | 31~60 | 28~42 |
| 3.5 | 32~60 | 27~40 |
| 4.0 | 31~60 | 27~40 |

Ranges Wi and Wp clearly seen by eyes with intraocular lenses of this embodiment and the conventional art respectively, having near vision visual acuities 0.3 or greater for each aperture diameter As shown above in FIG. 8(a) (b) (c) (d) and Table 2, the distance range clearly seen by an eye having near vision visual acuities 0.3 or greater is wider than that of the conventional art for each aperture diameter. Under various pupil conditions, in intermediate distance tasks such as reading and using personal computers, an aphakic patient with intraocular lens 10 of this embodiment can see a near distance object more easily and more clearly than an aphakic patient with intraocular lens 100 of the conventional art.

Visual acuity of 0.5 or greater is required for seeing an object at distance 60 cm to 1.5 m in front of eye (intermediate vision) and an object at distance 1.5 m to 6.0 m (far vision). FIG. 8(a) (b) (c) (d) and Table 3 show the comparison between the range Xi clearly seen by an eye with the intraocular lens 10 of this embodiment having intermediate vision and far vision visual acuities 0.5 or greater and the range Xp clearly seen by an eye with the intraocular lens 100 of the conventional art having intermediate vision and far vision visual acuities 0.5 or greater for each aperture diameter (2.5, 3.0, 3.5, and 4.0 mm).

TABLE 3

| Aperture diameter (mm) | Embodiment example Distance range Xi | Conventional art Distance range Xp |
| --- | --- | --- |
| 2.5 | 105~600 | 124~600 |
| 3.0 | 104~600 | 134~600 |
| 3.5 | 80~600 | 136~600 |
| 4.0 | 85~600 | 115~600 |

Ranges Xi and Xp clearly seen by eyes with intraocular lenses of this embodiment and the conventional art respectively having far vision visual acuities 0.5 or greater for each aperture diameter As shown above in FIG. 8(a) (b) (c) (d) and Table 3, the distance range clearly seen by an eye having intermediate vision and far vision visual acuities 0.5 or greater is wider than that of the conventional art for each aperture diameter of 2.5, 3.0, 3.5, and 4.0 mm. Results given in Tables 2 and 3 show that for various diameters, the intraocular lens of this embodiment has a deeper depth of focus of both near vision and far vision. Additionally, FIGS. 8(a) (b) (c) and (d) show the distance-visual acuity characteristics of the intermediate vision of this embodiment for various aperture diameters are higher than those of the conventional art.

Further, the distance-MTF value graph for spatial frequency 50 c/mm that corresponds to the visual acuity of 0.5 for each aperture diameter (2.5, 3.0, 3.5, and 4.0 mm) was obtained. Results of comparing this embodiment and the conventional art are shown in FIG. 9(a) (b) (c) (d) and Table 4 in which the MTF value of 0.05 or greater was used as the threshold value of the image quality (contrast and visibility), where an image still can be seen.

TABLE 4

| Aperture diameter (mm) | The embodiment | | Conventional art | |
| --- | --- | --- | --- | --- |
| | Far distance = 0.05 (MTF value) | Near distance = 0.05 (MTF value) | Far distance = 0.05 (MTF value) | Near distance = 0.05 (MTF value) |
| 2.5 | 114~600 | 49~60 | 135~600 | 34~36 |
| 3.0 | 120~600 | 33~60 | 143~600 | 30~39 |
| 3.5 | 146~600 | 31~44, 51~60 | 156~600 | 31~45 |
| 4.0 | 121~600 | 35~44, 51~60 | 130~600 | 31~39 |

Ranges of far distance and near distance of this embodiment and the conventional art where MTF value is equal to or greater than 0.05 in the distance-MTF value graphs shown in FIGS. 9(a) (b) (c) and (d) for each aperture diameter.

From the above results, comparing far distance and near distance of this embodiment and the conventional art at the condition of spatial frequency 50 c/mm that corresponds to the visual acuity of 0.5, when a human eye seeing an object and a background was set to MTF value of 0.05 or greater, the threshold value of the image quality (contrast and sharpness) where an image still can be seen, shows that the ranges are wider for this embodiment than those of the conventional art and the image quality (contrast and sharpness) is favorable for this embodiment than that of the conventional art. In addition, similar to the results shown in FIG. 8(a) (b) (c) (d), Table 2 and Table 3, the aforementioned results also show that the depth of focus of the near vision and the depth of focus of the far vision of this embodiment are deeper than the depth of focus of the near vision and the depth of focus of the far vision of the conventional art.

Further, in addition to the aforementioned method for reducing halo and glare symptoms, to absorb blue light component from near-ultraviolet which is the stimulus light component, an ophthalmic lens is colored and/or is made to have UV-absorbing capability by adding colorant and/or UV-absorber. Thus, reduction of halo and glare symptoms is achieved.

In addition, human crystalline lens is known to turn yellowish with aging, and when a transparent lens is implanted after removing the crystalline lens, the lens provides a suppressive effect for cyanopsia, being a chromosomal due to difference in color between the transparent lens and the human crystalline lens, change of a color perception, deterioration of contrast sensitivity, and an impact of the UV-ray on retina.

Moreover, elution of the colorant and UV-absorber used in coloring, is preferably minimized or to none from the ophthalmic lens. Therefore, reducing the contents of colorant and the UV-absorber is preferable, or using the reactive dye and the reactive UV-absorber that combines with an ophthalmic lens material is more preferable.

Preferable examples of colorant described in color index (CI) are; oil soluble dyes such as CI solvent yellow and CI solvent orange, or disperse dyes such as CI disperse yellow and CI disperse orange. The colorant other than the aforementioned examples may also be acceptable, provided that it has good compatibility with the lens material.

As yellowish colorants, CI solvent yellow 16, CI solvent yellow 29, CI solvent yellow 33, CI solvent yellow 44, CI solvent yellow 56, CI solvent yellow 77, CI solvent yellow 93, CI disperse yellow 3, etc, are given.

Additionally, as yellowish brown colorants, CI solvent yellow 14, CI solvent yellow 104, CI solvent yellow 105, CI solvent yellow 110, CI solvent yellow 112, CI solvent yellow 113, CI solvent yellow 114, etc, are given.

Further, as orangish colorants, CI solvent orange 60, CI solvent orange 67, CI solvent orange 68, CI solvent orange 79, CI solvent orange 80, CI solvent orange 86, CI disperse orange 47, are given.

As particularly preferable colorants of the aforementioned colorants, CI solvent yellow 93, CI solvent yellow 44, CI solvent yellow 16, CI solvent yellow 77, CI disperse yellow 3, etc, are given. This is because they are compounds, with maximum absorption wavelengths set in a range of near 350 to 400 nm. Namely, these colorants have absorption of visible light from 400 to 500 nm, and have an advantage of simultaneously absorbing the light from 300 to 400 nm, a UV-absorbing range of the crystalline lens.

In addition, as the desirable reactive colorant, a pyrazolone-based reactive yellow dye expressed by (formula 1) described in Japanese Patent Laid Open Publication No.10-195324, and a pyrazolone-based reactive dye expressed by (formula 2) described in Japanese Patent Laid Open Publication No.2000-290256. This is because the aforementioned dies are combined with a material of the multifocal ophthalmic lens and are not eluted from the lens. In the following formula, X illustrates a phenyl group or a 4-alkyl phenyl group.

[Formula 1]

Formula 1

[Formula 2]

(I)

HMPO—H: X; (phenyl)

HMPO—M: X; $H_3C$—(phenyl)

HMPO—B: X; $H_3C$—$C(CH_3)_2$—(phenyl)

In the multifocal ophthalmic lens of this embodiment, by using the UV-absorber together with the colorant, arbitrary adjustment is possible so as to absorb light ray in a range from 300 to 400nm. As such a UV-absorber, (1) Benzotriazole Group
2-(2'-hydroxy-3'-tert-butyl-5'-methylphenyl)-5-chlorobenzotriazole(TINUVIN 326 by CIBA-GEIGY Corporation)
2-(2'-hydroxy-5'-methylphenyl)benzotriazole(TINUVIN P by CIBA-GEIGY Corporation)
2-(2'-hydroxy-3',5'-ditert-butylphenyl)benzotriazole (TINUVIN 320 by CIBA-GEIGY Corporation)
2-(2'-hydroxy-3',5'-ditert-butylphenyl)-5-chlorobenzotriazole Triazole (TINUVIN 327 by CIBA-GEIGY Corporation)
2-(2'-hydroxy-3',5'-ditert-amylphenyl)benzotriazole (TINUVIN 328 by CIBA-GEIGY Corporation)

(2) Benzophenone Group
2,4-dihydroxybenzophenone
2-hydroxy-4-methoxybenzophenone
2-hydroxy-4-octoxybenzophenone
2-hydroxy-4-dodecyloxybenzophenone
2,2'-dihydroxy-4-methoxybenzophenone
2,2'-dihydroxy-4,4'-dimethoxybenzophenone
2-hydroxy-4-methoxy-5-sulfobenzophenone (3) Salicylate
Phenyl salicylate
p-tert-butylphenyl-salicylate
p-octylphenyl salicylate are given.

Also it is possible to use, a reactive UV-absorber having a chemical structure partially similar to that of the aforementioned UV-absorbers, and having a part copolymerizable with a monomer applied for a base material of the intraocular lens. For example, UV-absorbers composed of 2-hydroxy-4-acrylyloxyethoxybenzophenone, 2-(2-hydroxy-4-methacryloyloxyethoxy)-4-chlorobenzotriazole, and benzotriazole compound shown in (formula 3) described in Japanese Patent Laid Open Publication No.08-311045, are preferable. Also, as the other benzotriazole-based reactive UV-absorber, the reactive UV-absorber having the following structural formula shown in (formula 4) described in Japanese Patent Laid Open Publication No.2000-290256 is preferable. In the formula, X indicates a hydrogen atom, halogen atom, C1 to C4 alkyl groups or C1 to C4 alkoxy group.

[Formula 3]

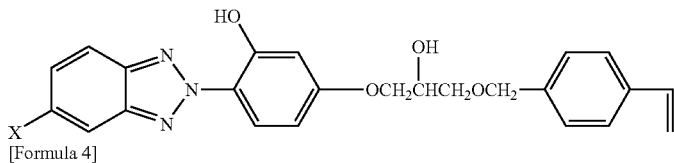

[Formula 4]

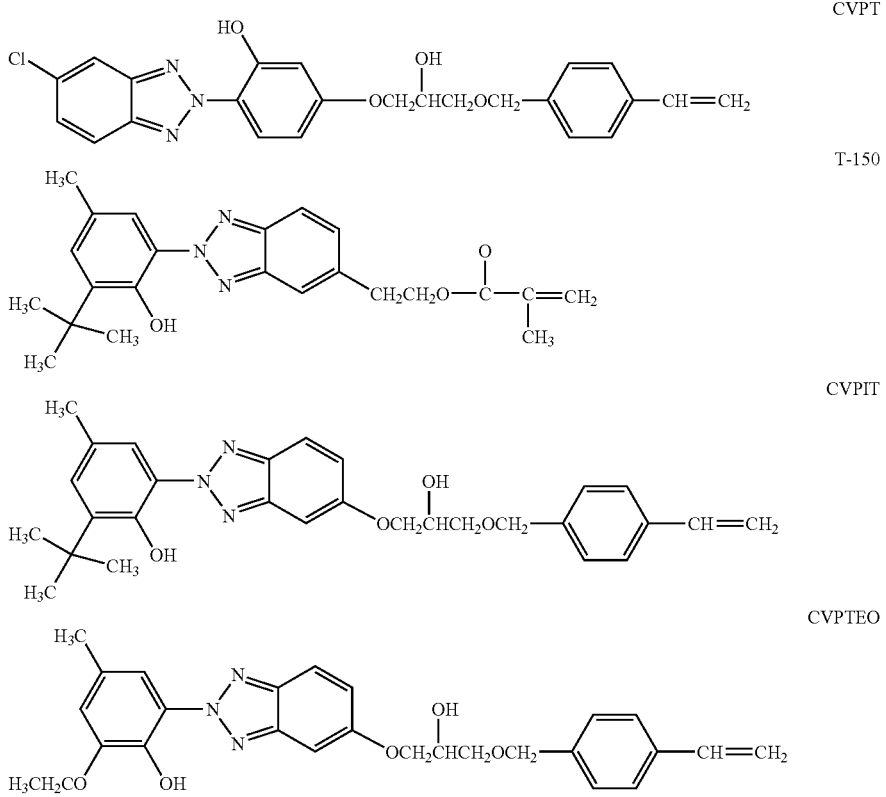

As a transparent lens material used in the ophthalmic lens having a multifocal structure of this embodiment, for example, a hard polymer material, and a hydrophilic and hydrophobic soft polymer material are given.

The hard polymer material is not particularly limited if it is mainly composed of methyl methacrylate, and the hydrophilic soft material is not particularly limited if it is mainly composed of 2-hydroxymethyl methacrylate, and the hydrophobic soft material is not particularly limited if it has rubber elasticity and has characteristics as a soft lens material.

As a silicone-based material, one-component and two-component type liquid silicone rubber that cures by condensation and an addition reaction, can be given, and as an acrylic material, for example, methyl methacrylate and long chain acrylate or methacrylate (n-butylacrylate, n-hexylacrylate, n-octylacrylate, nonylacrylate, laurylacrylate, stearylacrylate, 2-ethylhexyl methacrylate, nonyl methacrylate, lauryl methacrylate, stearyl methacrylate, etc) can be given.

The copolymer obtained by copolymerizing the aforementioned main components under existence of crosslinking agents (ethylene glycol dimethacrylate, arylmethacrylate, trimethylolpropane trimethacrylate, etc) is possible to use.

As the soft lens material, one kind or two kinds of the long chain acrylate or methacrylate are used, with preferable glass transition temperature of 30° C. or less. In addition, as the monomer copolymerized with metylmethacrylate, monomers such as fluorine-containing acrylate and fluorine-containing methacrylate can be selected.

As an example of the multifocal ophthalmic lens of this embodiment, 1.5 wt % of UV-absorber T-150 and 0.02 wt % of reactive yellow dye HMPO-H contained in the compound of a general formula (I) were added to a mixture of n-butylacrylate (n-BA) 42 g, phenylethyl methacrylate (PEMA) 52 g, perfluoro octylethyloxy propylene methacrylate (HRM-5131HP) 8 g, ethylene glycol dimetacrylate (EDMA) 5 g, and AlBN 0.33 g, then the mixture was sufficiently stirred while flowing nitrogen gas, and the obtained polymerizable material was placed into a polypropylene (PP) resin mold for ophthalmic lens, which was then heated from a room temperature to 60° C. for 30 minutes, held for 12 hours at 60° C., heated from 60° C. to 90° C. for 15 minutes, then held for 3 hours at 90° C., heated for 15 minutes from 90° C. to 100° C., held for 12 hours at 100° C., and thereafter thermally polymerized based on a polymerization program in which the temperature was naturally decreased to room temperature. The obtained polymer was cut, to form the multifocal ophthalmic lens of this embodiment. Light transmittance measurement was performed to this multifocal ophthalmic lens, and a light transmittance curve was obtained from a mean value of 10 lenses as shown in FIG. 23(A). Further, the multifocal ophthalmic lens of this example was formed by excluding the reactive yellow dye from the aforementioned composition. Thus, the light transmittance curve was obtained from the mean value of the transmittance of 10 multifocal ophthalmic lenses (FIG. 23(B)), then compared with the light transmittance curve of the lens containing the reactive yellow dye. Here, FIG. 23 describes as a comparative example, the light transmittance of the human crystalline lens (Citation: Source of human crystalline lens, Boettner EA et al: "Transmission of the ocular media" Invest. Ophthalmol 1:776 to 783, 1962).

As a result, light transmittance curve (B) of the lens containing only UV-absorber, shows that the light of an ultraviolet region of 400 nm or less is absorbed. Also, light transmittance curve (A) using the reactive yellow dye is more closer to a human crystalline lens curve than the light transmittance curve (B) containing only the UV-absorber, and found UV-light from blue light from 500 nm to 400 nm, a stimulus light component of halo and glare symptoms, was absorbed to realize reduction of halo and glare symptoms.

[B] Second Embodiment (FIG. 10)

FIG. 10 is an illustration of lens body 31 of an intraocular lens of the second embodiment, an ophthalmic lens according to the present invention, wherein FIG. 10(A) is a front view, and FIG. 10(B) is a graph showing the power distribution in radial direction of the lens.

The intraocular lens 30 of the second embodiment includes a lens body 31 and support members that are not shown, and near zone 32 is arranged in the center zone of an optical region of the lens body 31, and an annular far zone 33 is arranged concentrically outside the region of the near zone 32.

The near zone 32 is a region for correcting the near vision, and the far zone 33 is a region for correcting the far vision. In addition, in these near zone 32 and the far zone 33, the power distribution in the entire region in radial direction (the near zone 32 is arranged in a range from point 0 to point d, and the far zone 33 is arranged in a range from point d to point e shown in FIG. 10(B)) is progressively changed, and the depth of focus of near vision provided by the near zone 32 and the depth of focus of far vision provided by the far zone are extended. In addition, power is altered discontinuously at the boundary (point d in FIG. 10(B)) between the near zone 32 and the far zone 33 where the stepwise power difference between near power of the near zone 32 and far power of the far zone 33 has no intermediate power.

The near zone 32 is set to have a value less than the addition power (3 to 4 D) prescribed for a patient as a proper power for correcting near vision of the patient. Also, the far zone 33 is set to have a mean power value greater than and positive relative to a reference power (0 D) in the inner sub-region, namely the sub-region next to the near zone 32 of the far zone 33. Further, the far zone 33 is set have a mean power value that is equal to or less than and negative relative to the reference power in the outer sub-region of the lens.

By designing the optical configuration of intraocular lens 30 as described above, the effects similar to the effects mentioned in (1) to (3) of the embodiments can be obtained.

As described above, the present invention has been explained based on the aforementioned embodiments, however the present invention is not limited thereto. For example, in aforementioned embodiments, the total number of far zones and near zones for correcting visual acuity in the optical zone of intraocular lens is three (first far zone 13, near zone 14, and second far zone 15) for the first embodiment, and two (near zone 32 and far zone 33) for the second embodiment, however a total number of four or five or more far zones and near zones may also be arranged alternatively.

Moreover, other embodiments are given in the followings.
(1) In the embodiment 1, the nearest distance of intermediate distance was set to 60 cm. However, the nearest distance can be set to a value greater or smaller than this distance. Also, the farthest distance of intermediate distance was set to 1.5 m. However, the farthest distance can be set to a value greater or smaller than this distance.
(2) In the embodiment 1, the power is set to be altered discontinuously to have a stepwise power difference at the boundary between the near zone and the far zone. However, power may also be abruptly altered from a maximum intermediate power to a minimum intermediate power at the boundary between the near zone and the far zone.
(3) In the embodiment 1, the ophthalmic lens of three-zone type having the first far zone, the near zone, and the second far zone is shown, the mean power of center zone or the first far zone may have the same or similar value with the value of the mean power of the second annular region or the second far zone.

Also, in the aforementioned embodiment, the ophthalmic lens was explained is in the case of the intraocular lens for an aphakic eye, however the ophthalmic lens can also be an intraocular lens for a phakic eye, a contact lens, an intraocular contact lens, and eyeglasses. In the case of contact lens, by setting the mean power at the boundary at the inflection point, the change of curvature in the transition part is smoothed, and foreign body sensation when contacting with eyelid is reduced, then comfort in wearing is improved, and the effect of eyeball movement to lens fitting can be reduced. Thus, the image quality of far vision of the eye of lens wearer is improved, the possibilities of halo and glare symptoms in a dark environment is reduced and make easier manufacturing. Also, in the case of contact lens, the comfort of wearing is improved and the effect to lens fitting can be reduced.

BRIEF DESCRIPTION OF THE DRAWINGS

FIG. 4 is an illustration of a comparison of the depth of focus of the intraocular lens according to the first embodiment shown in FIG. 1 and FIG. 2, and the depth of focus of the intraocular lens according to the conventional art, wherein FIG. 4(A) illustrates a case of the intraocular lens of the conventional art, and FIG. 4(B) illustrates a case of the intraocular lens according to the first embodiment.

FIG. 5 is an illustration of a comparison of a far point and a near point of the intraocular lens according to the first embodiment shown in FIG. 1 and FIG. 2, and a far point and a near point of the intraocular lens according to the conventional art, wherein FIG. 5(A) illustrates a case of the intraocular lens of the conventional art, and FIG. 5(B) illustrates a case of the intraocular lens according to the first embodiment.

FIG. 6 is an illustration of a comparison of halo symptom of the intraocular lens according to the first embodiment shown in FIG. 1 and FIG. 2, and halo symptom of the intraocular lens according to the conventional art, wherein FIG. 6(A) illustrates a case of the intraocular lens of the conventional art, and FIG. 6(B) illustrates a case of the intraocular lens according to the first embodiment.

FIG. 10 is a front view illustration of a lens body 31 of the intraocular lens, being a second embodiment of the ophthalmic lens according to the present invention, wherein FIG. 10(A) is a front view of the lens body 31 and FIG. 10(B) is a graph showing the power distribution in radial direction of the lens.

FIG. 11 is an illustration of a lens body of the intraocular lens according to the conventional art, wherein FIG. 11(A) is a side view and FIG. 11(B) is a front view.

FIG. 24 is an illustration showing the comparison of halo patterns in intraocular lens of this embodiment (aperture diameter 4.0 mm) and in intraocular lens of conventional art, wherein FIG. 24(a) represents the conventional art, and FIG. 24(b) represents this embodiment.

FIG. 25 is an illustration showing the comparison of halo patterns in intraocular lens of this embodiment (aperture diameter 5.0 mm), and in intraocular lens of conventional art, wherein FIG. 25(a) represents the conventional art, and FIG. 25(b) represents this embodiment.

Figure 1:
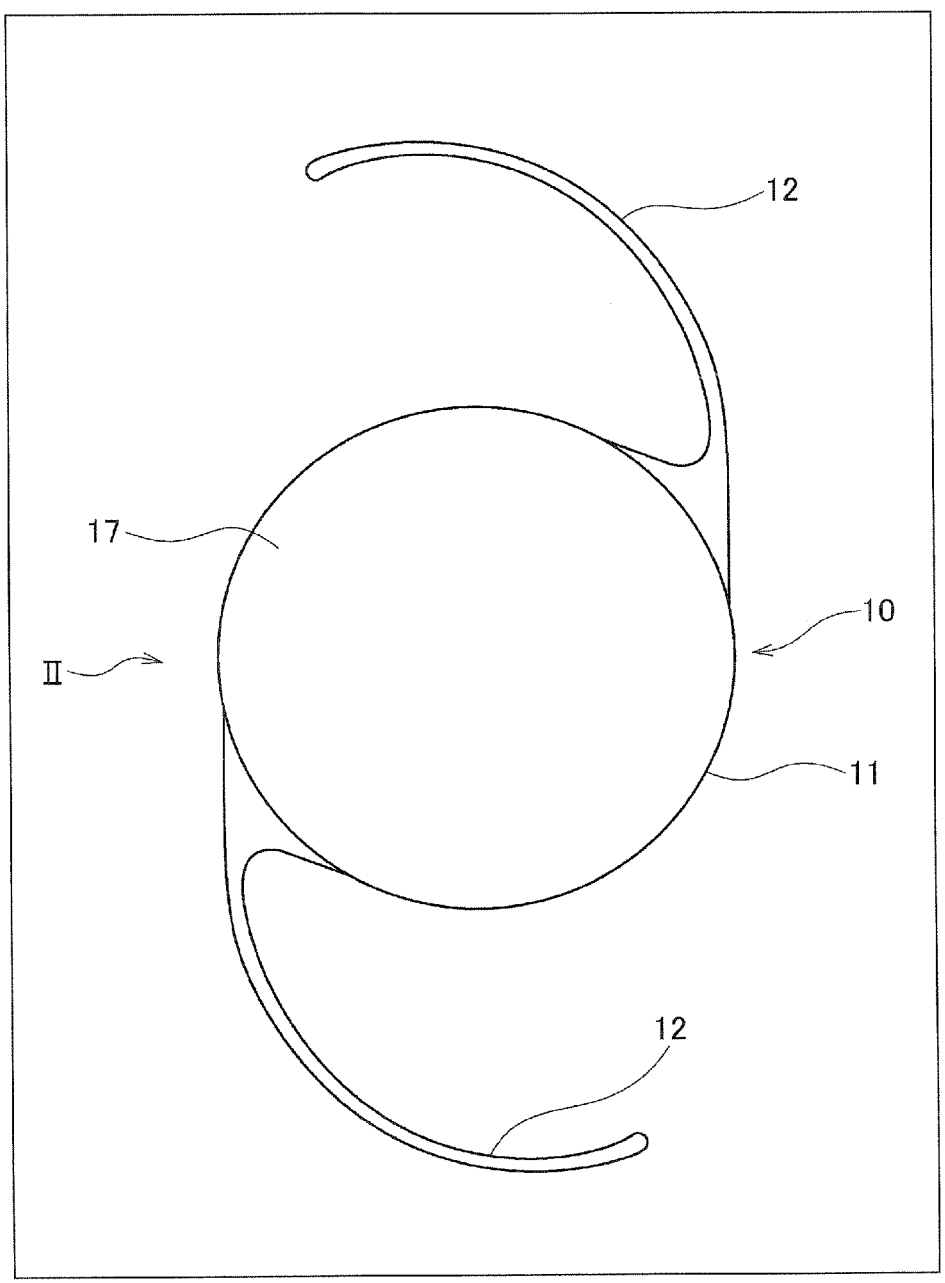
FIG. 1 is a front view illustration of an intraocular lens, being a first embodiment of an ophthalmic lens according to the present invention.
Figure 2:
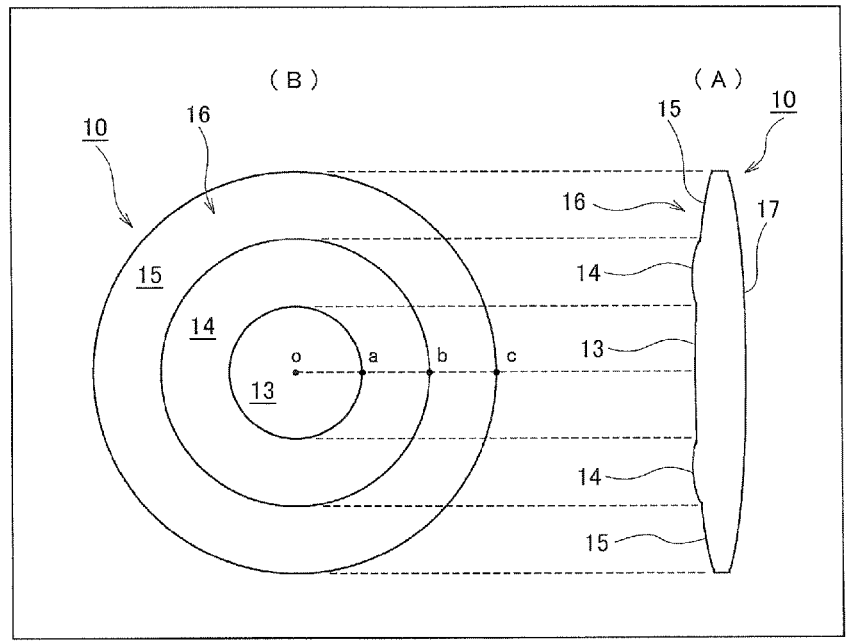
FIG. 2(A) is a side view illustration of the intraocular lens shown in FIG. 1.
FIG. 2(B) is a front view of an lens body 11 of the intraocular lens in FIG. 1.
Figure 3:
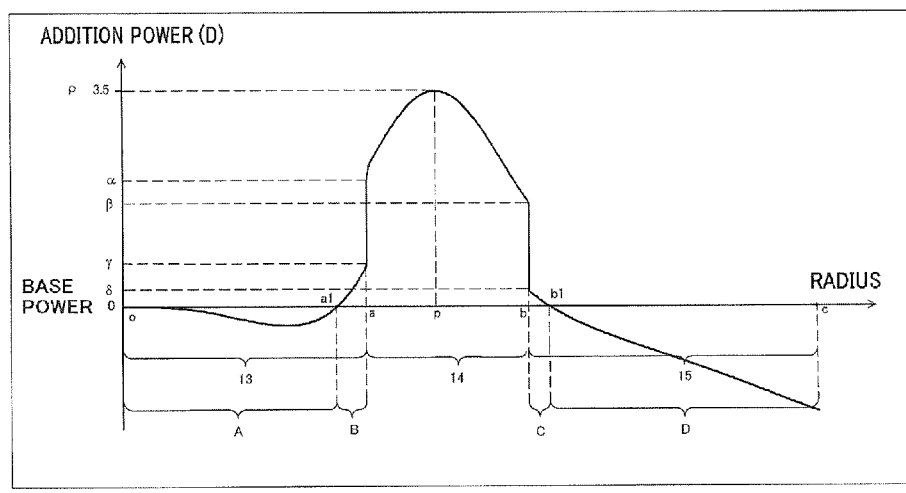
FIG. 3 is a graph showing a power distribution in radial direction of the lens of the lens body 11 of the intraocular lens shown in FIG. 1 and FIG. 2.
Figure 4:
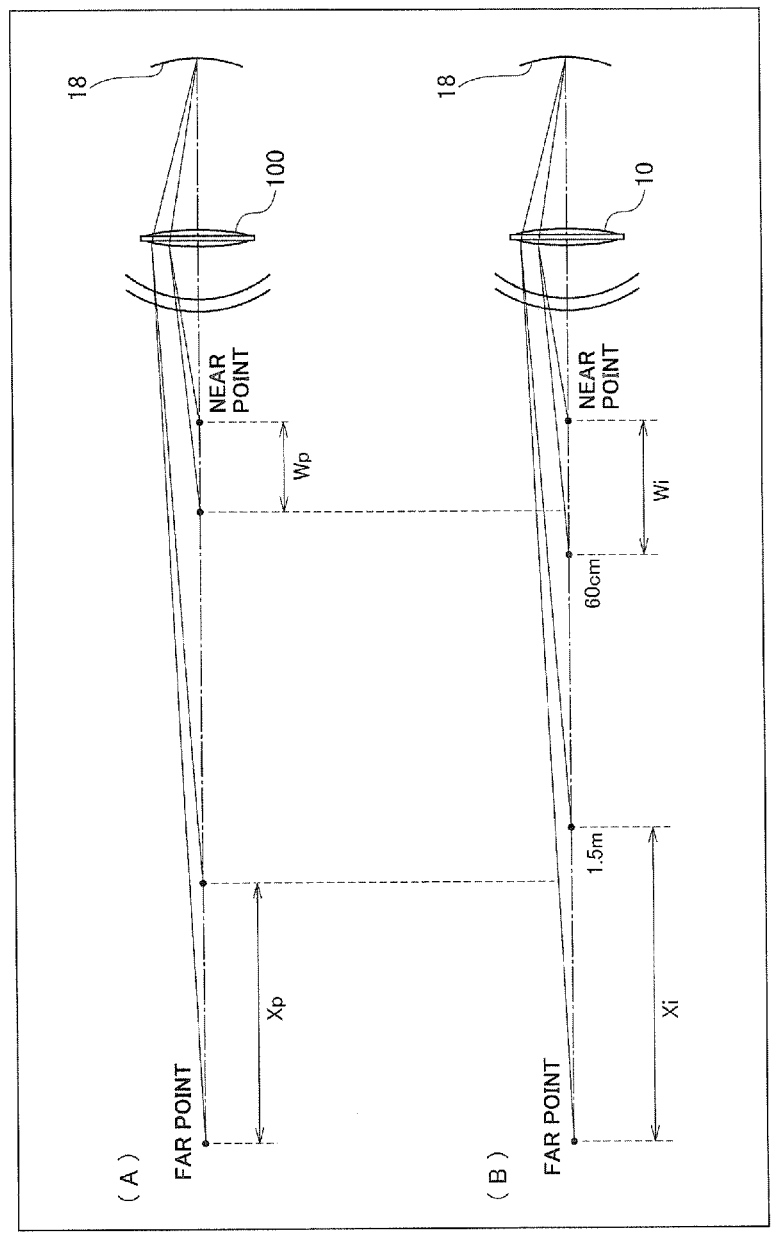
Figure 5:
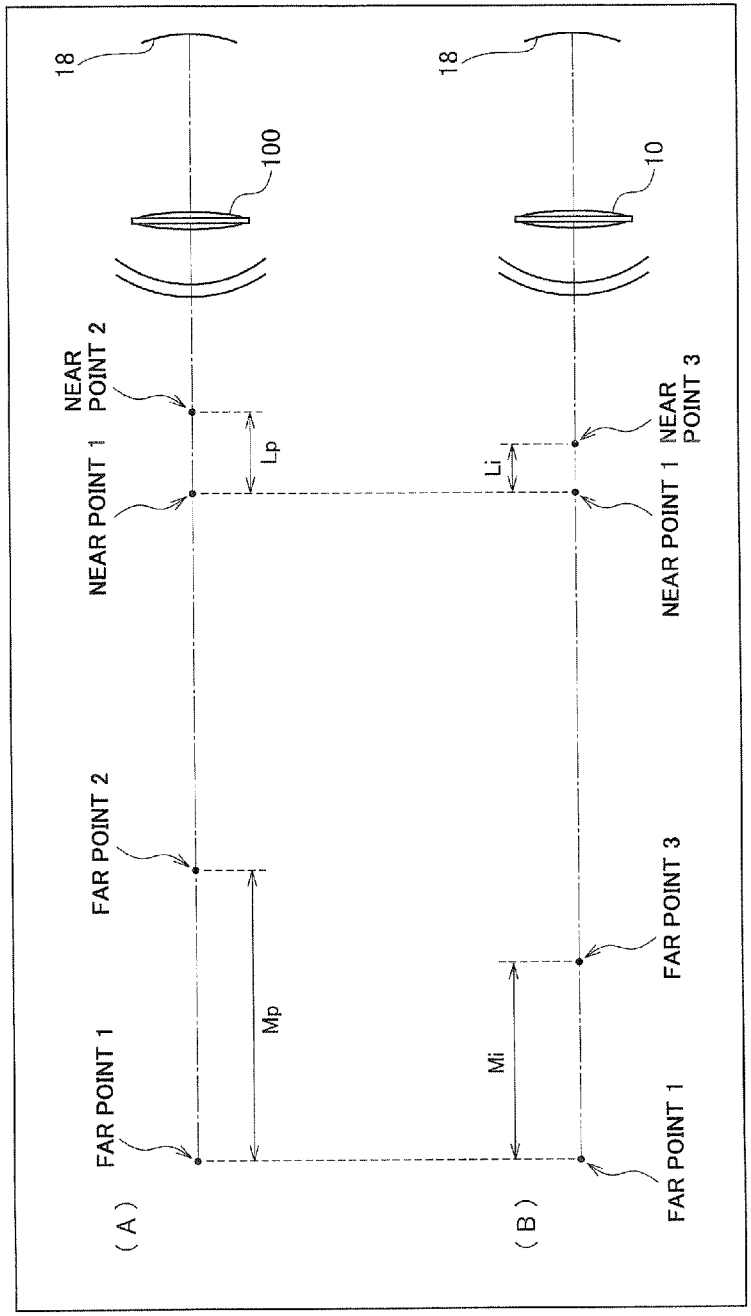
Figure 6:
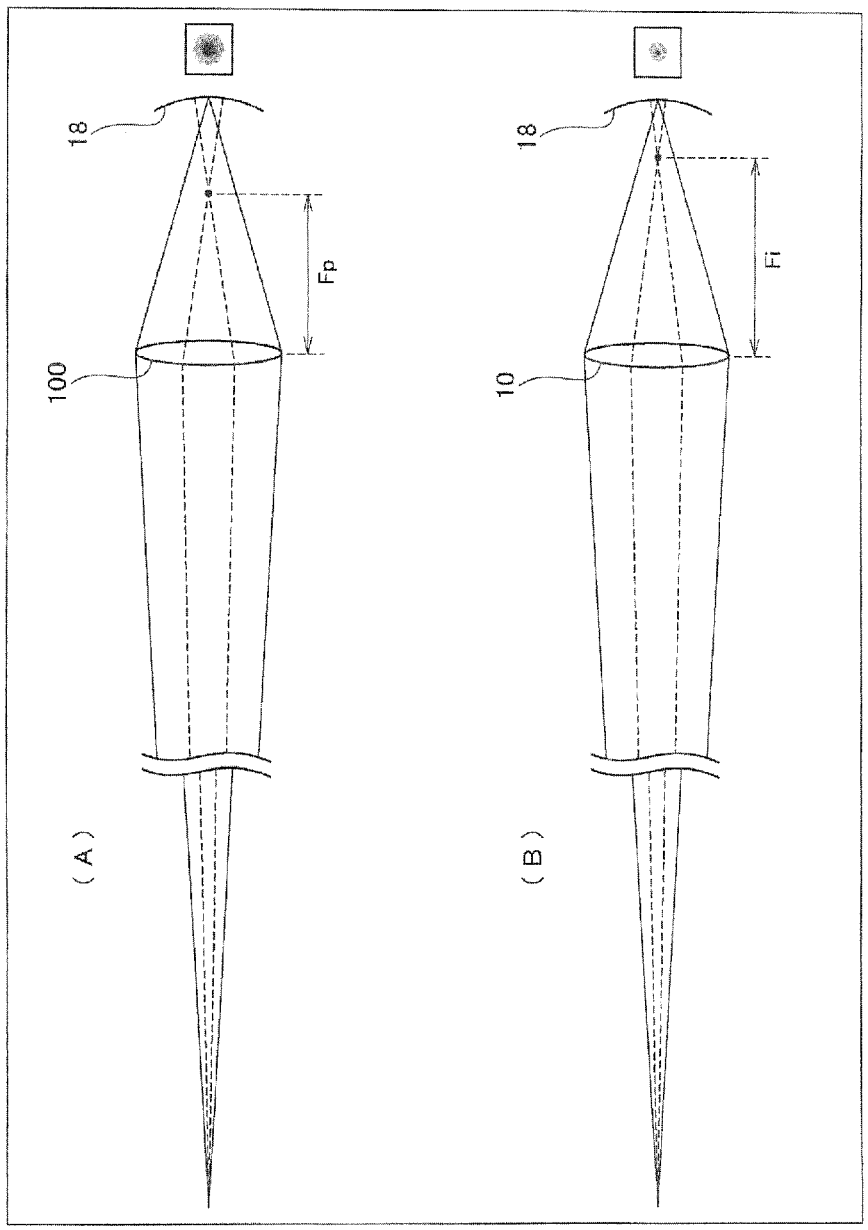
Figure 7:
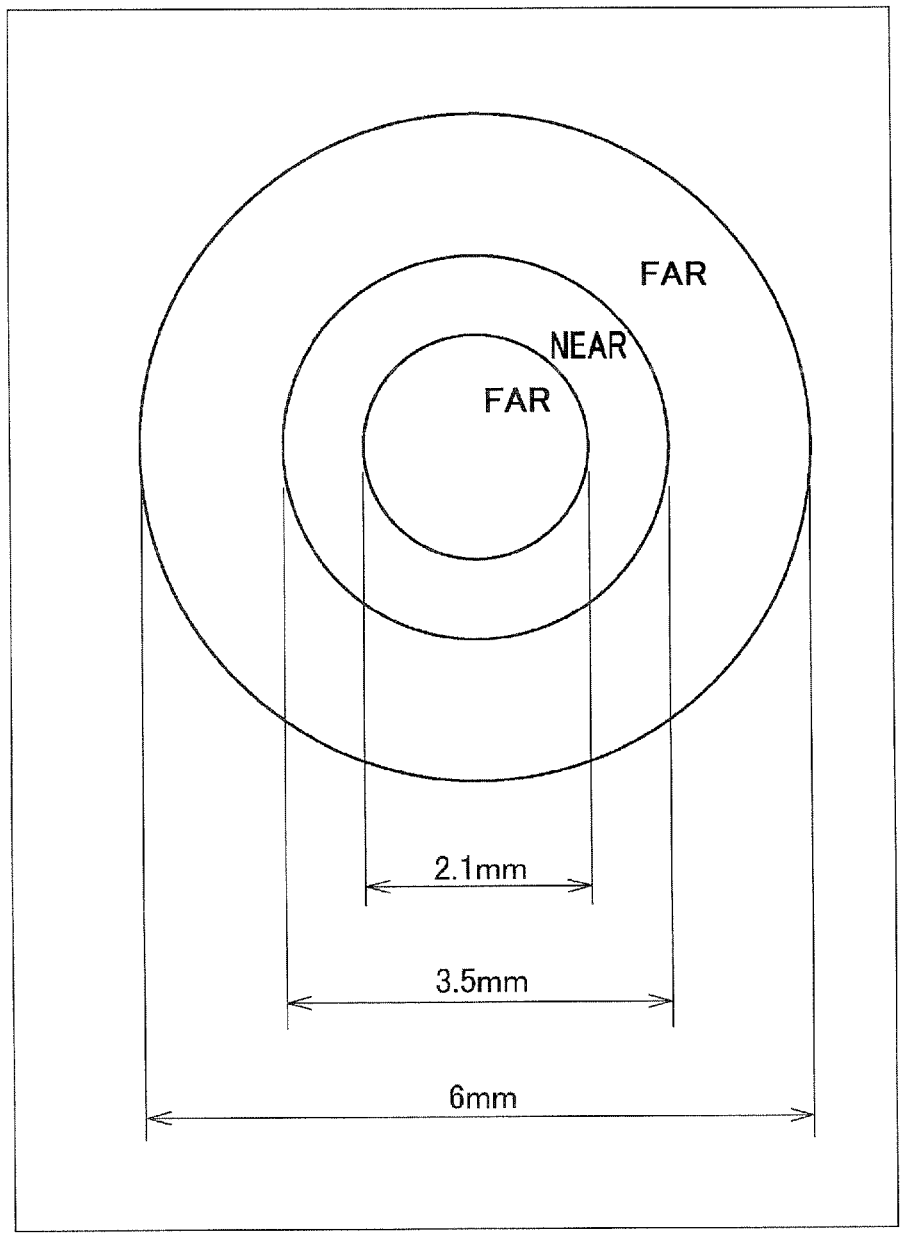
FIG. 7 is an illustration of the configuration of far zone and a near zone in a multifocal intraocular lens according to the first embodiment.
Figure 8:
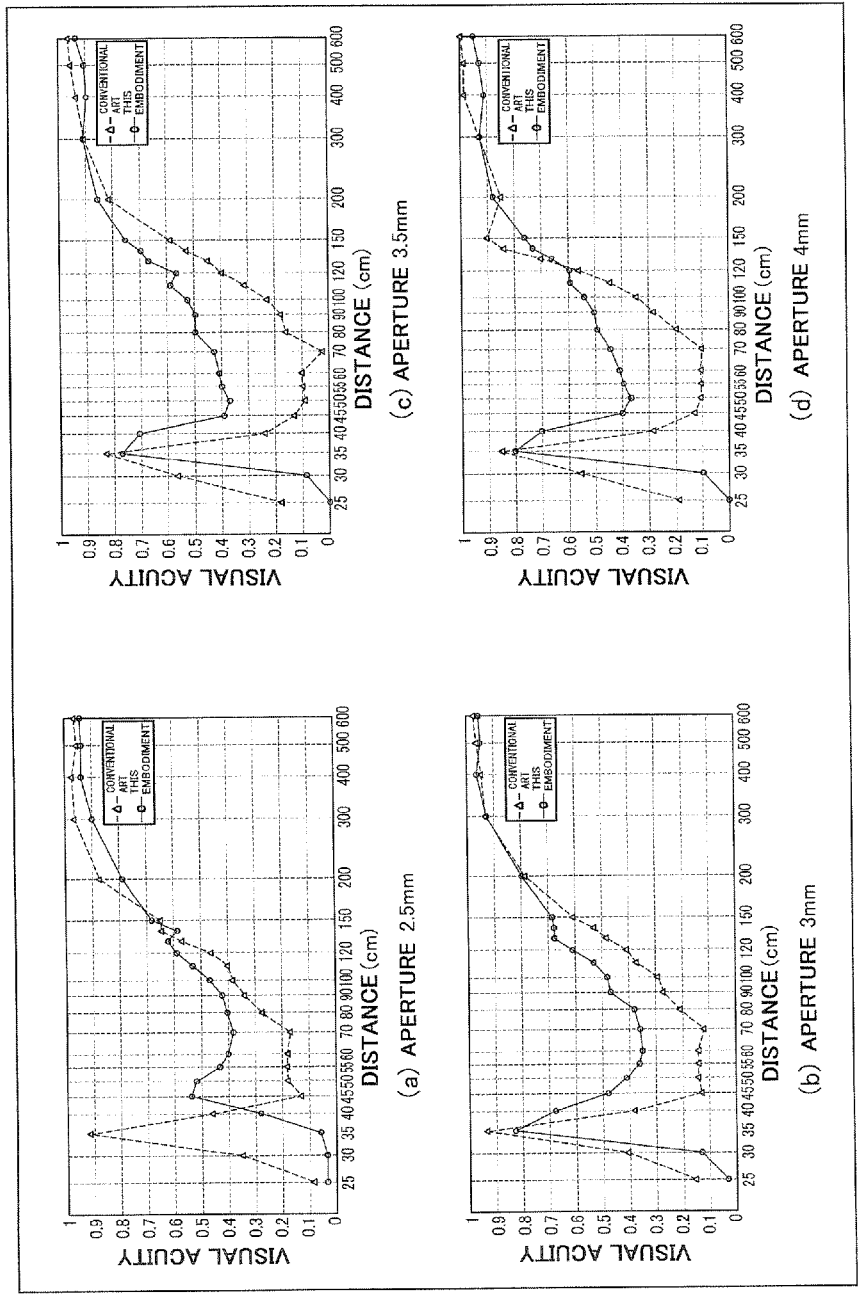
FIG. 8 is a graph showing distance-visual acuity characteristics of the intraocular lens in FIG. 1 and FIG. 2.
Figure 9:
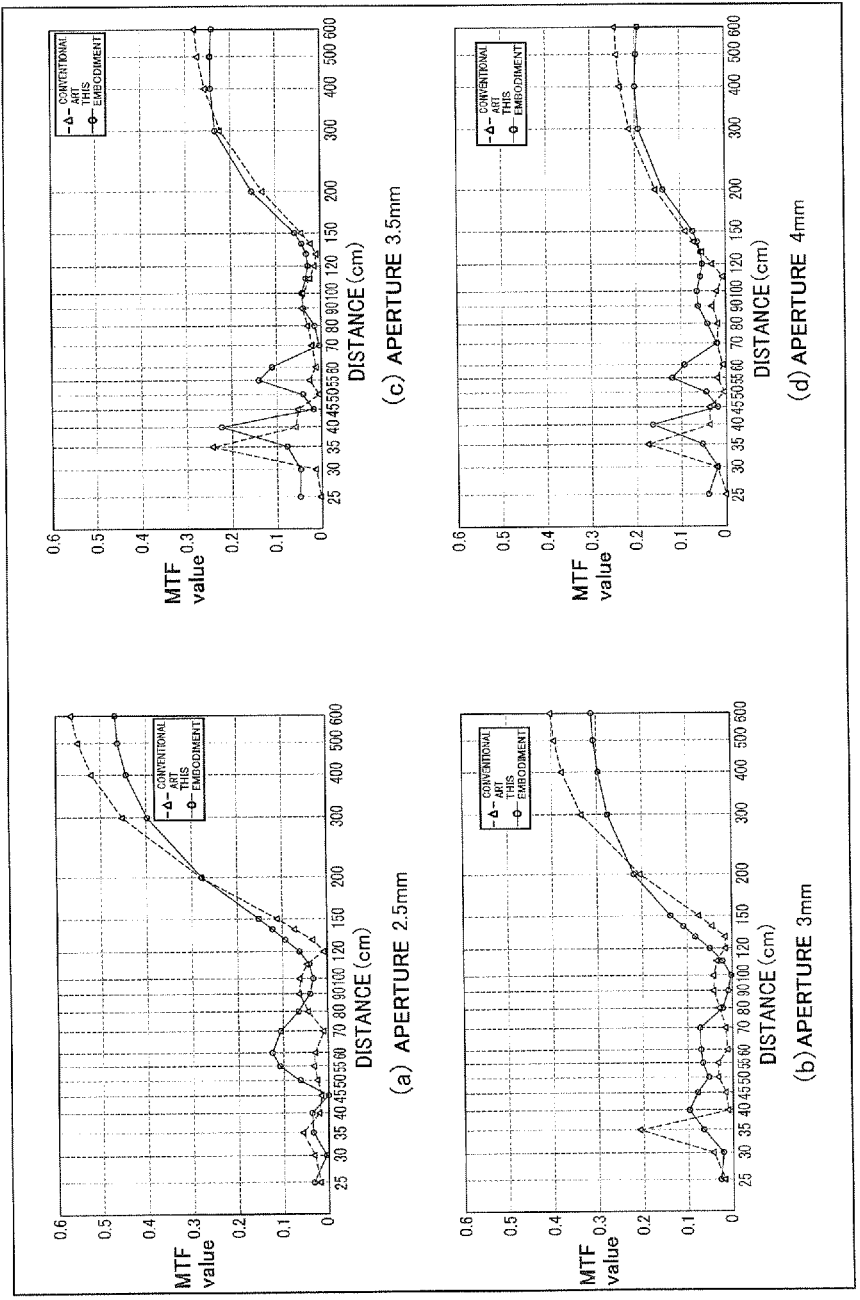
FIG. 9 is a graph showing distance-contrast characteristics of the intraocular lens in FIG. 1 and FIG. 2.
Figure 10:
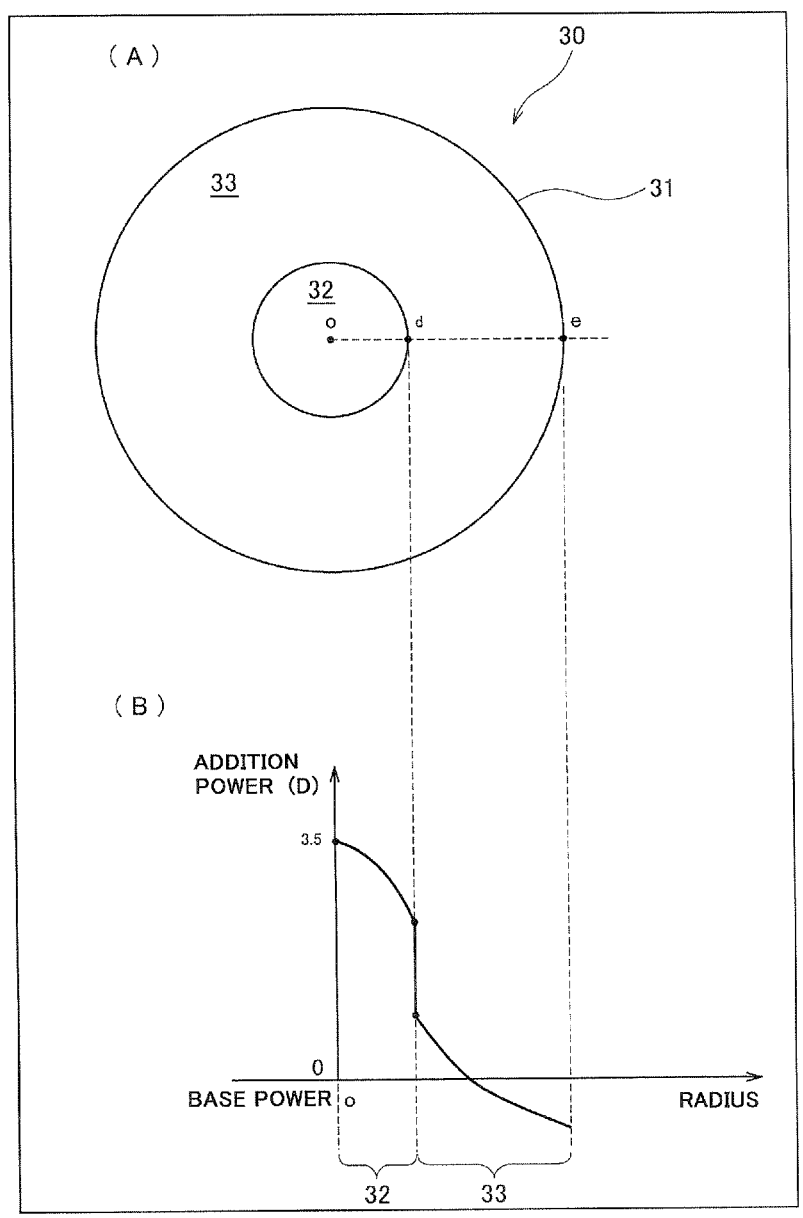
Figure 11:
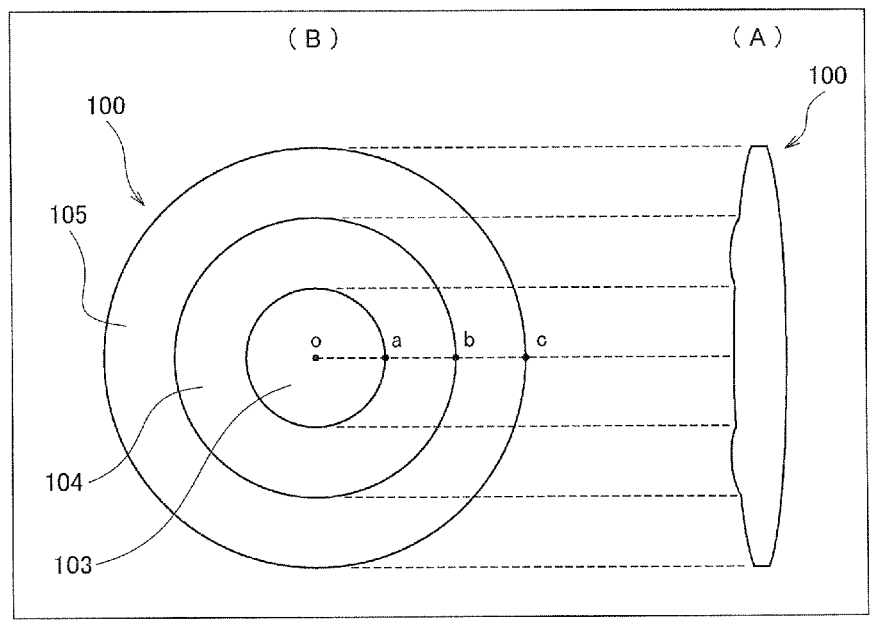
Figure 12:
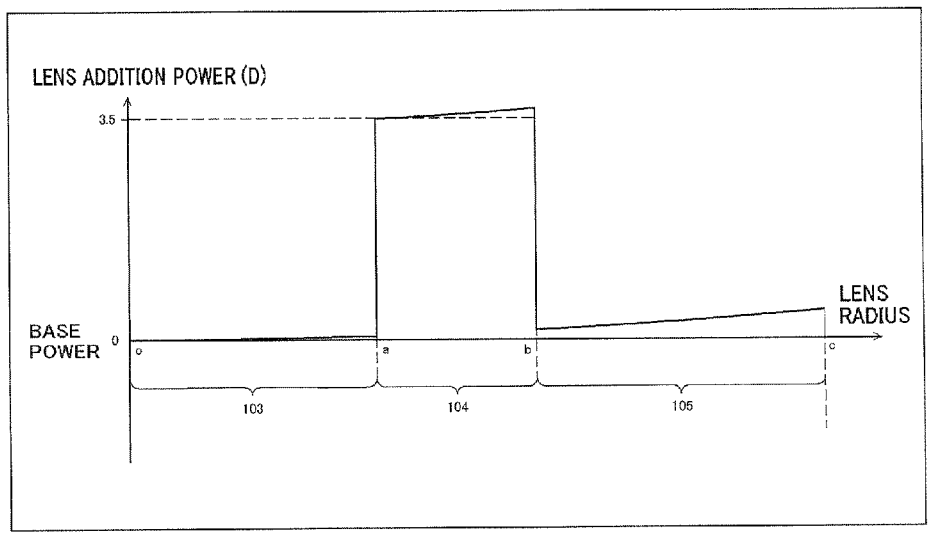
FIG. 12 is a graph showing the power distribution of the conventional intraocular lens shown in FIG. 11 in radial direction of the lens.
Figure 13:
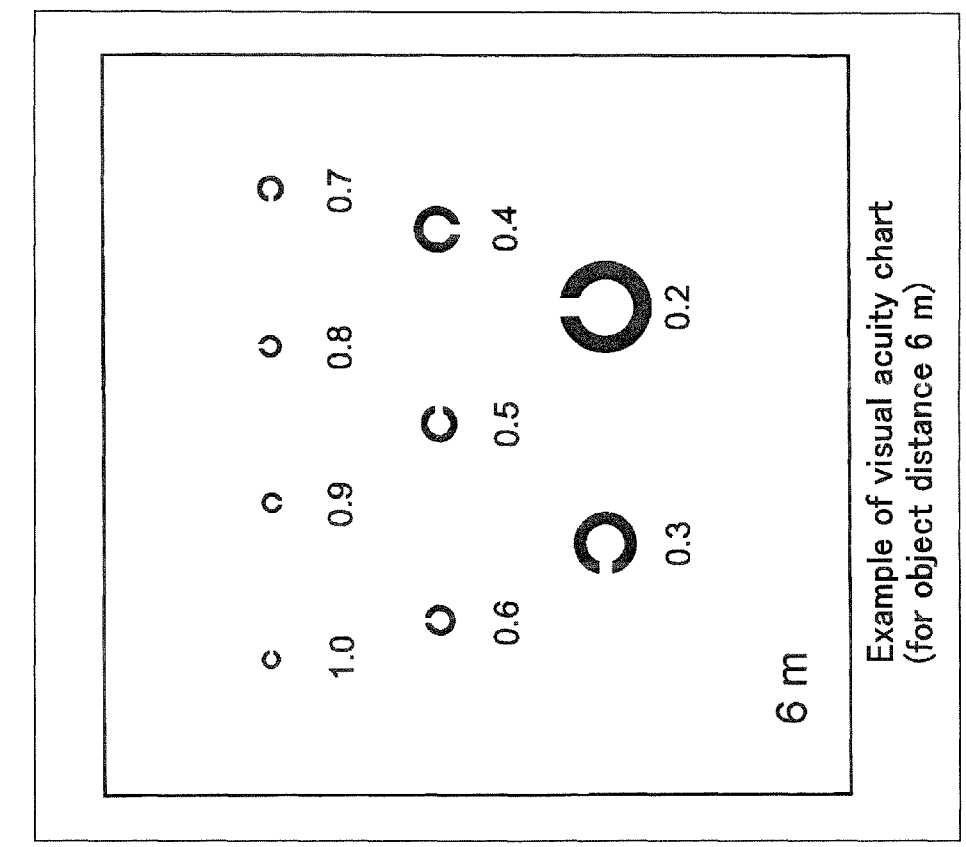
FIG. 13 is an illustration of Landolt ring visual acuity charts showing visual acuity from index 0.2 to index 1.0.
Figure 14:
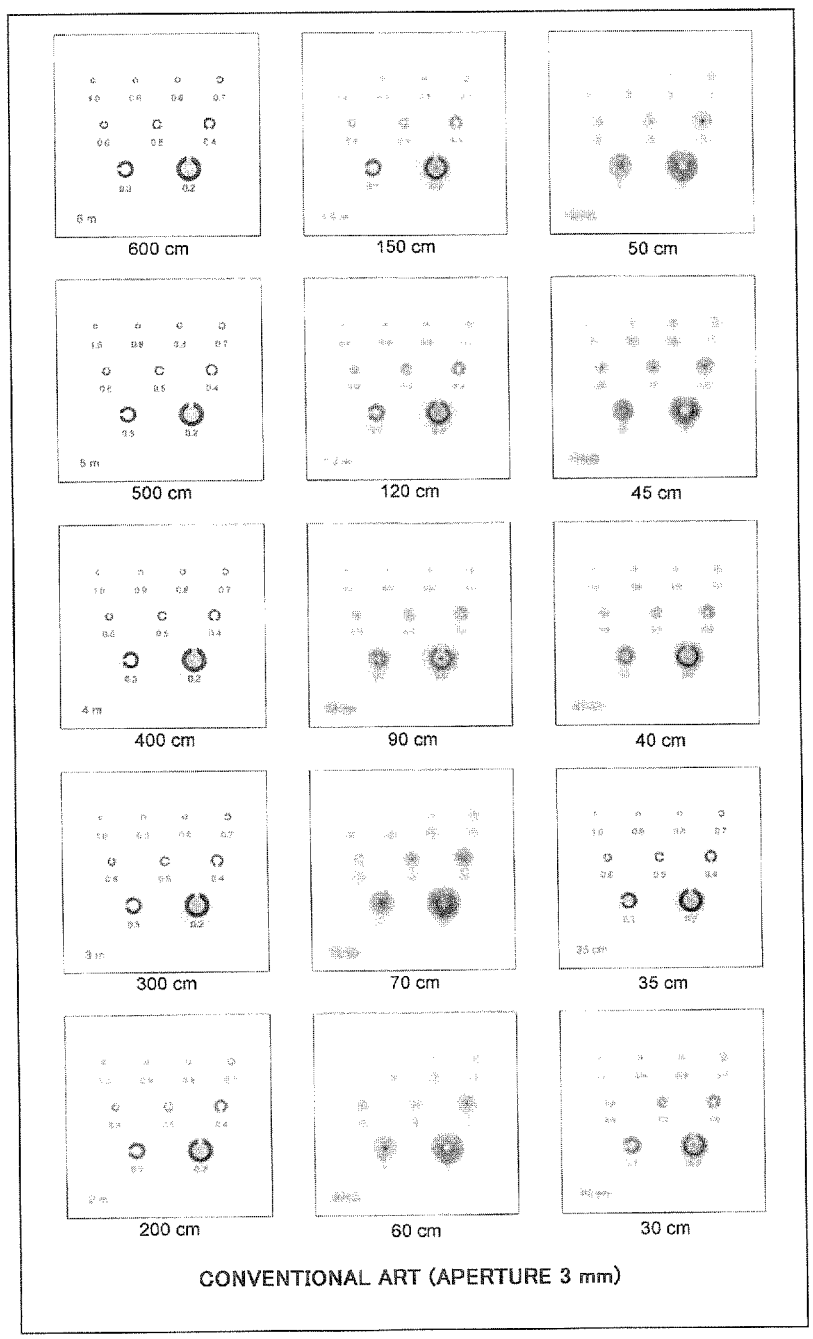
FIG. 14 is an illustration of sample images of simulation result for each distance, the image of visual acuity chart constructed by the intraocular lens 100 of the conventional art at each distance was simulated with ZEMAX for aperture diameter of eye model 3 mm.
Figure 15:
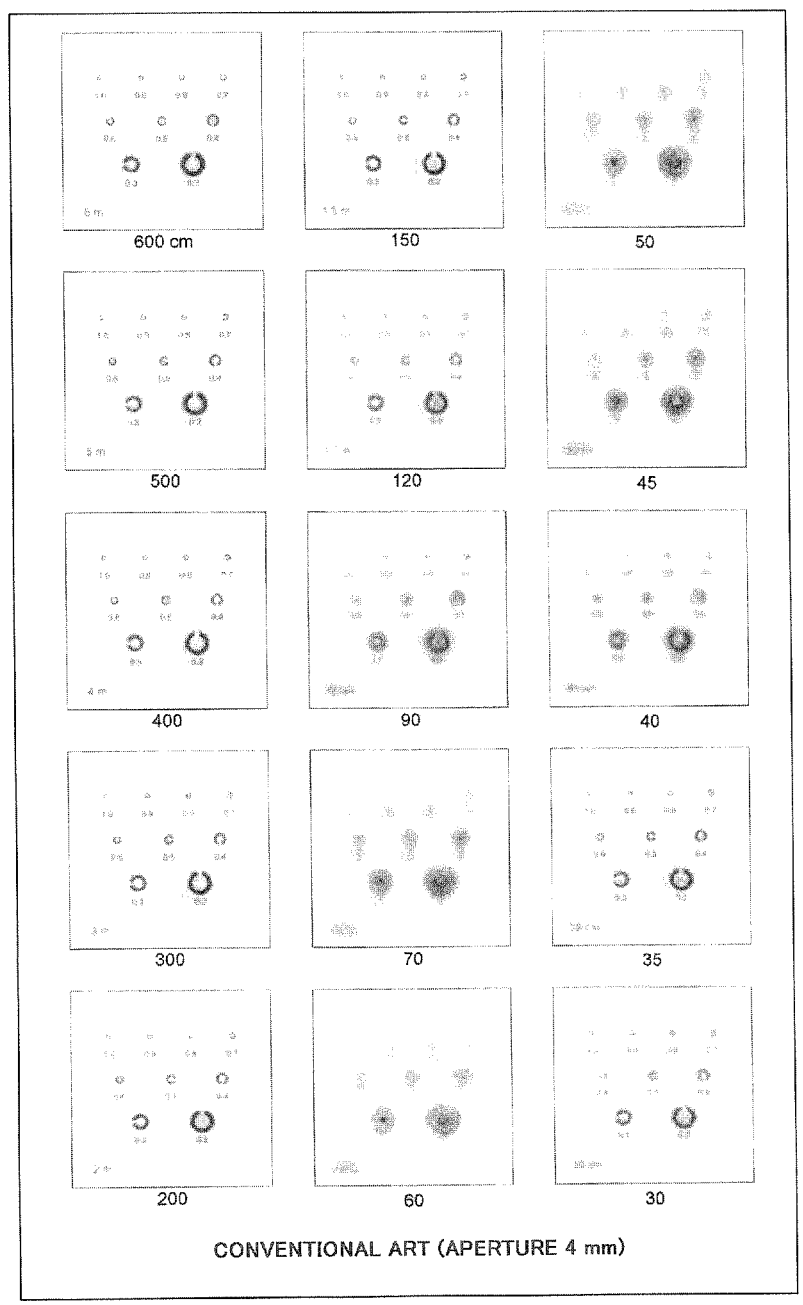
FIG. 15 is an illustration of sample images of simulation result for each distance, the image of visual acuity chart constructed by the intraocular lens 100 of the conventional art at each distance was simulated with ZEMAX for aperture diameter of eye model 4 mm.
Figure 16:
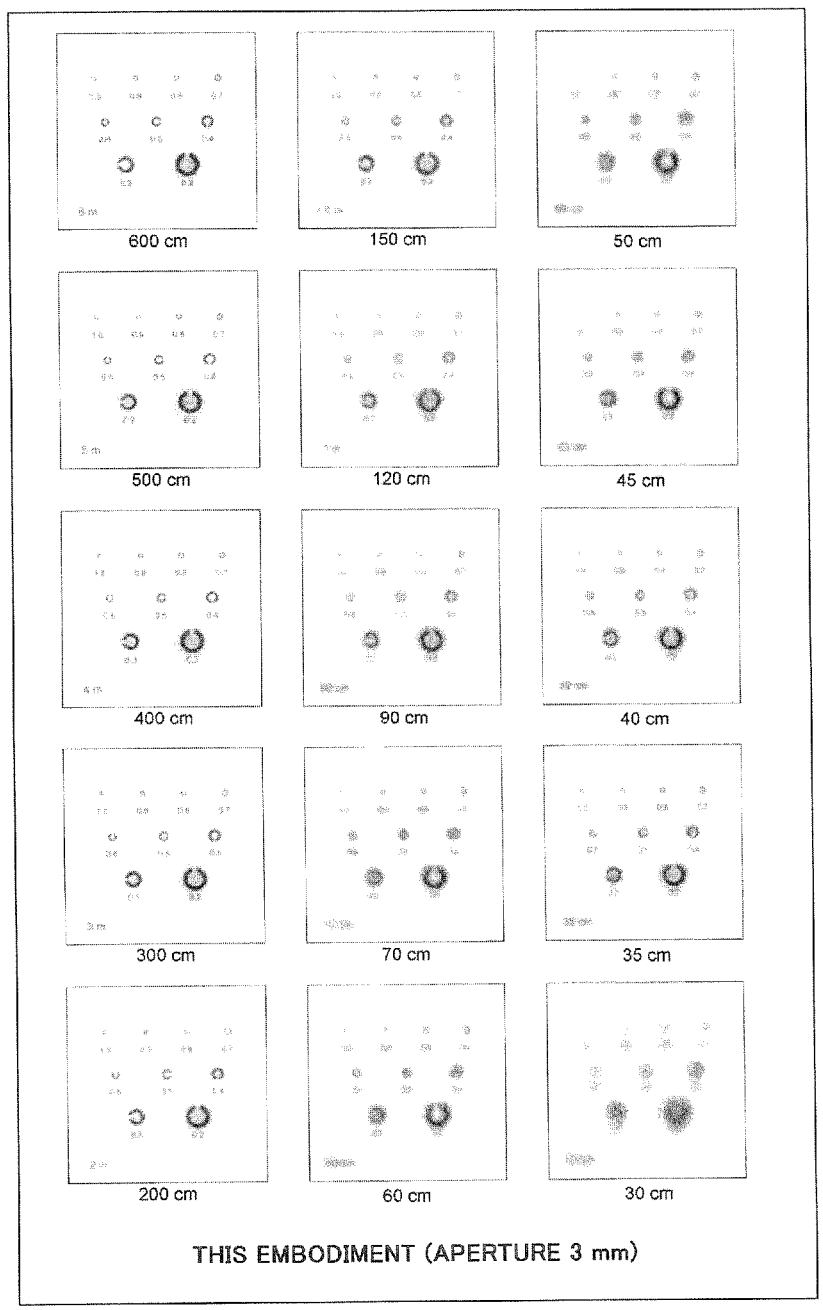
FIG. 16 is an illustration of sample images of simulation result for each distance, the image of visual acuity chart constructed by the intraocular lens 10 of the first embodiment at each distance was simulated with ZEMAX for aperture diameter of eye model 3 mm.
Figure 17:
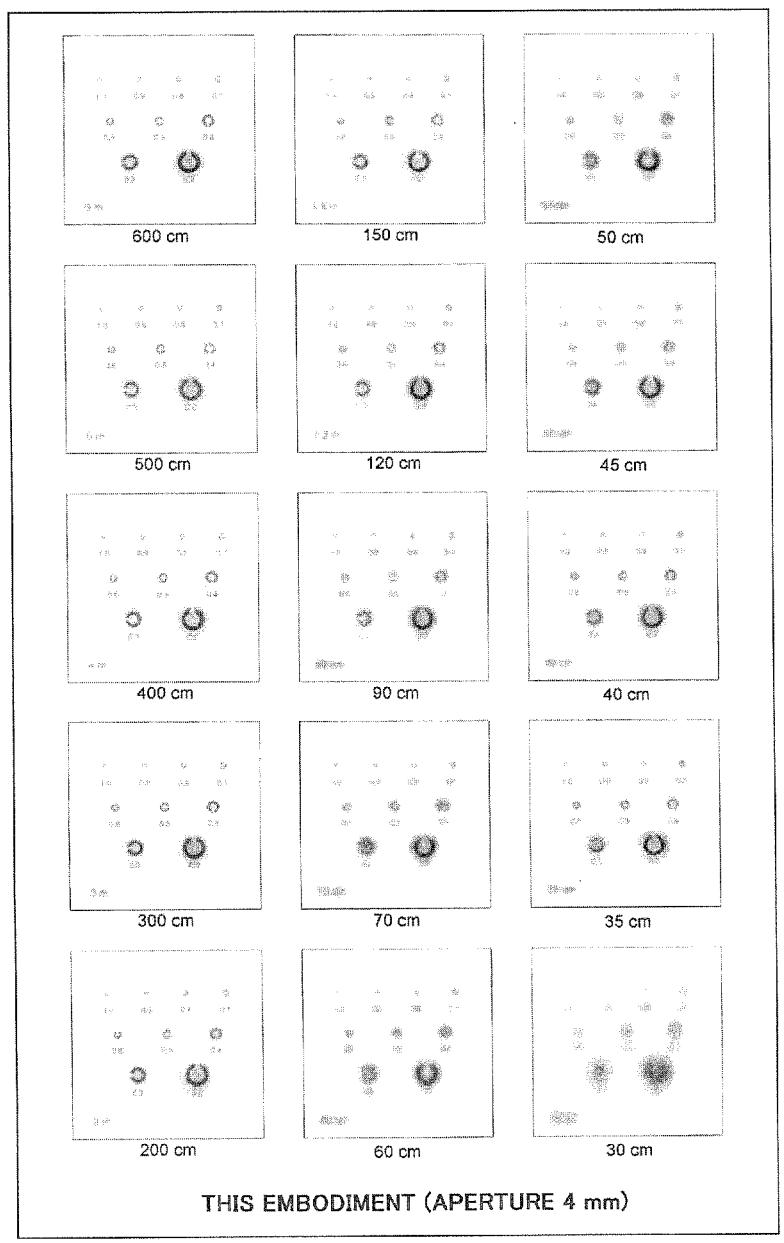
FIG. 17 is an illustration of sample images of simulation result for each distance, the image of visual acuity chart constructed by the intraocular lens 10 of the first embodiment at each distance was simulated with ZEMAX for aperture diameter of eye model 4 mm.
Figure 18:
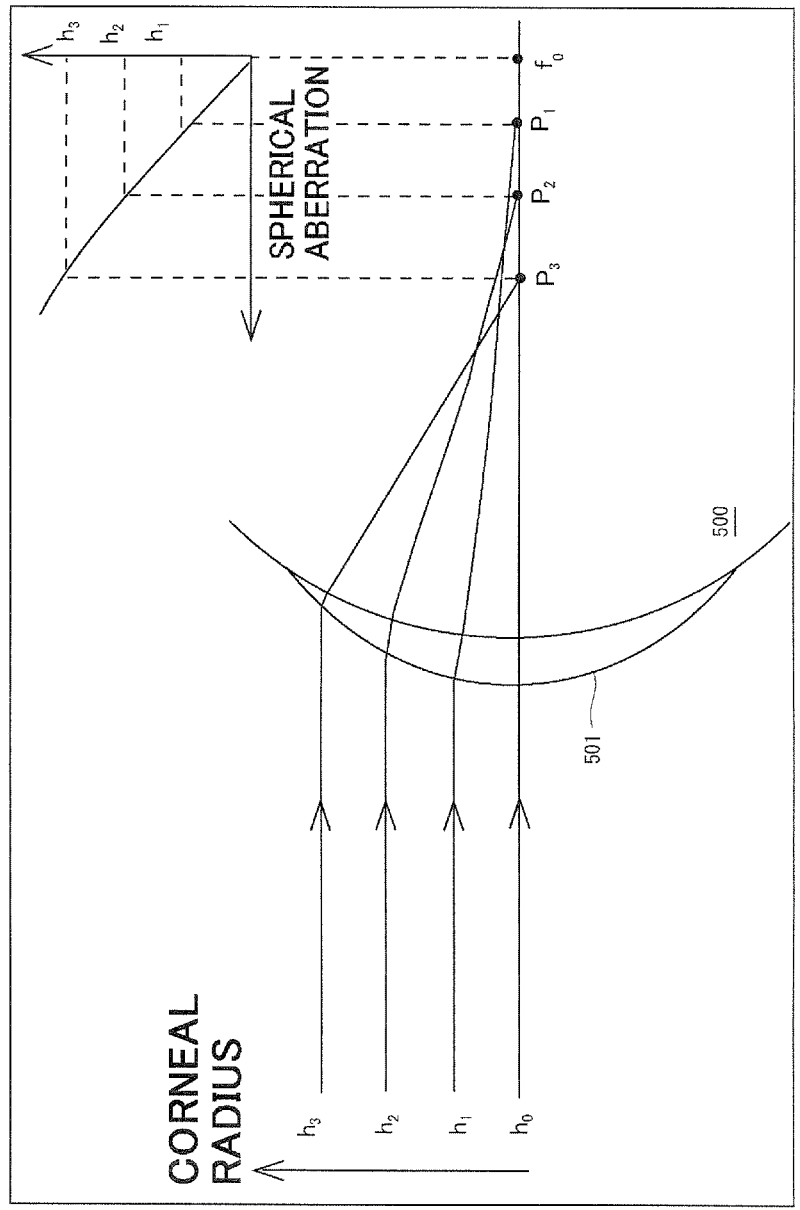
FIG. 18 is an illustration of a relation of refractive power or spherical aberration and radial height.
Figure 19:
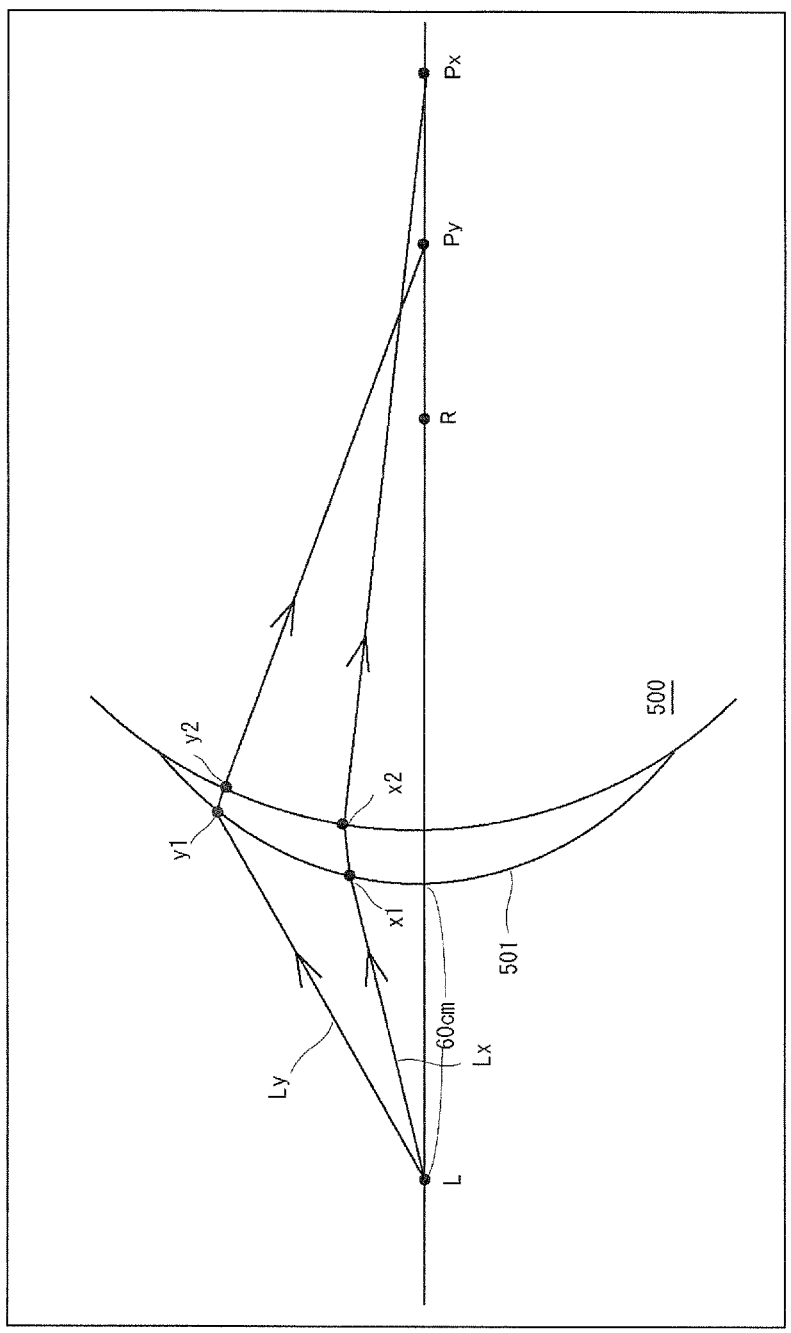
FIG. 19 is an illustration of the effect of refractive power or spherical aberration of cornea when a light source is positioned at 60 cm in front of the cornea.
Figure 20:
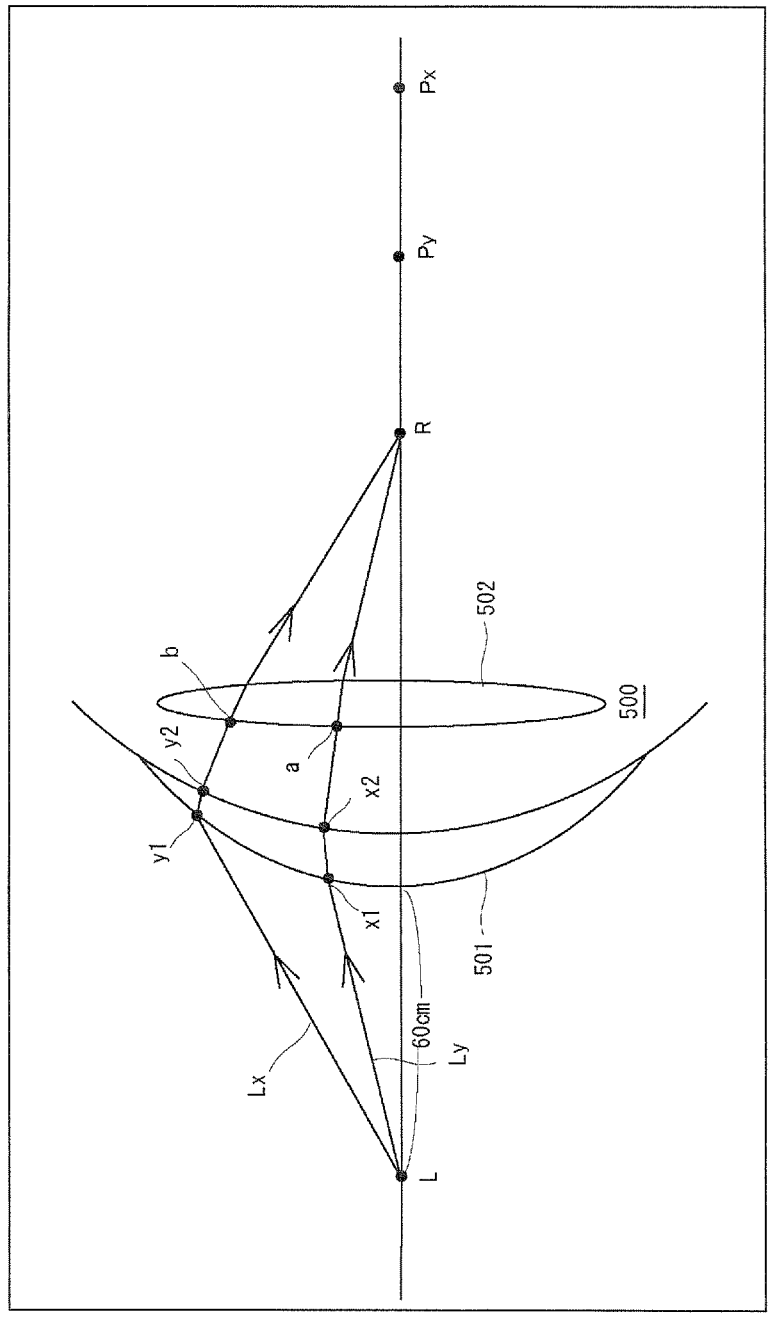
FIG. 20 is an illustration showing the light rays refracted by the cornea and the intraocular lens coincides on retina when a light source is positioned at 60 cm in front of the cornea.
Figure 21:
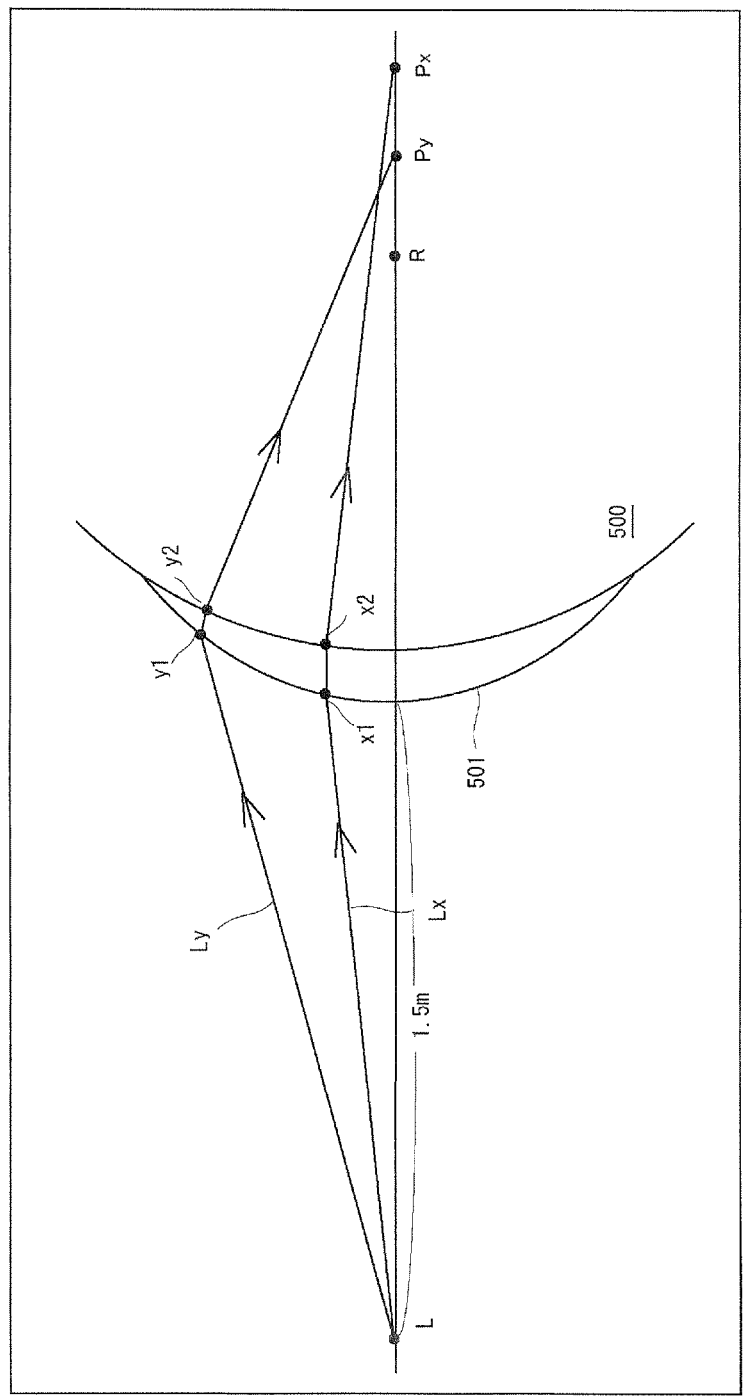
FIG. 21 is an illustration showing the effect of the refractive power or spherical aberration of cornea when a light source is positioned at 1.5 m in front of the cornea.
Figure 22:
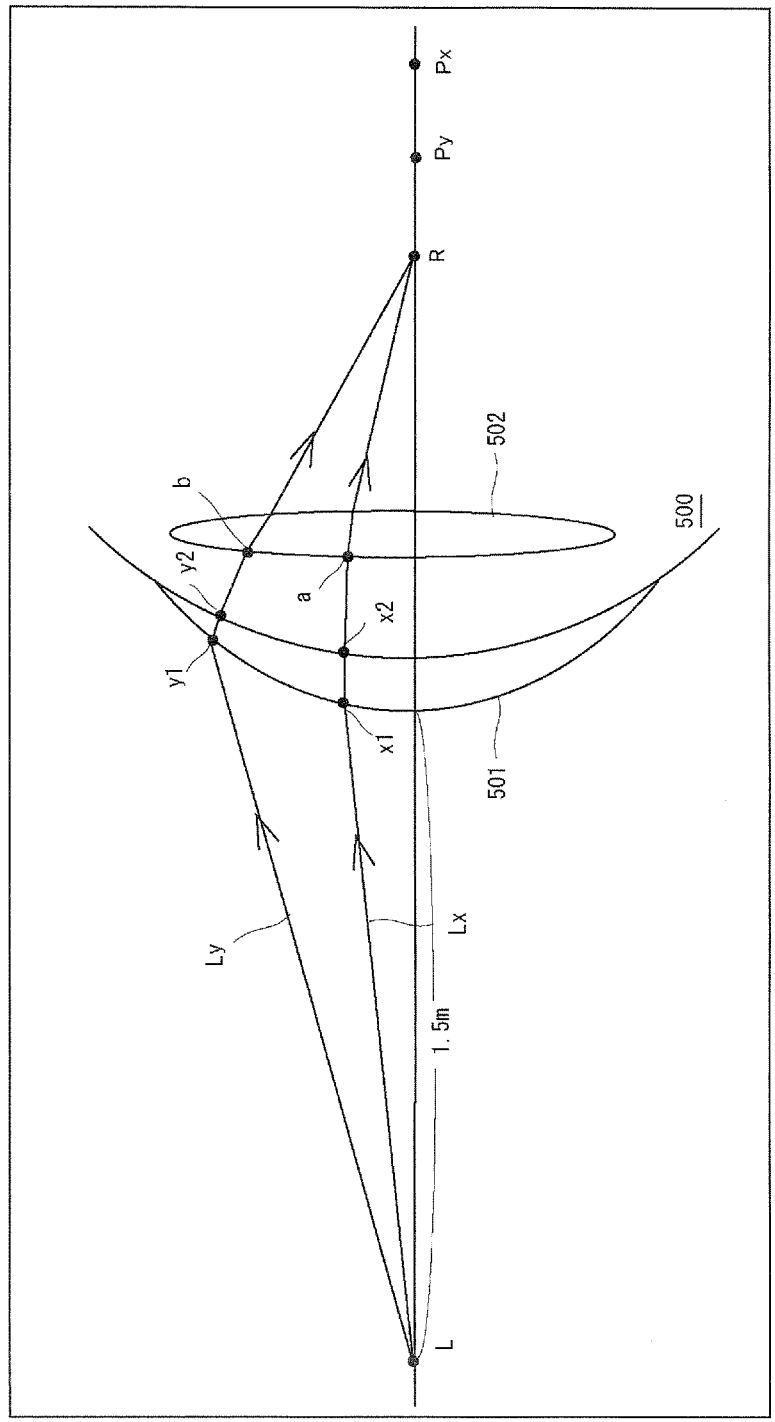
FIG. 22 is an illustration showing the light rays refracted by the cornea and the intraocular lens coincides on retina when a light source is positioned at 1.5 m in front of the cornea.
Figure 23:
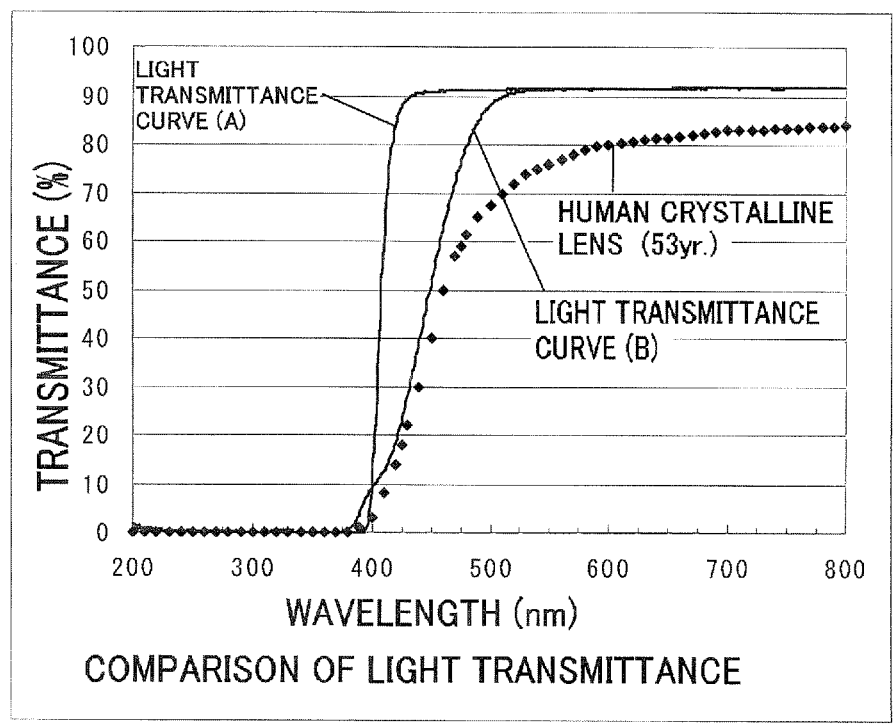
FIG. 23 is an illustration of the relation between wavelength and light transmittance in this embodiment.
Figure 24:
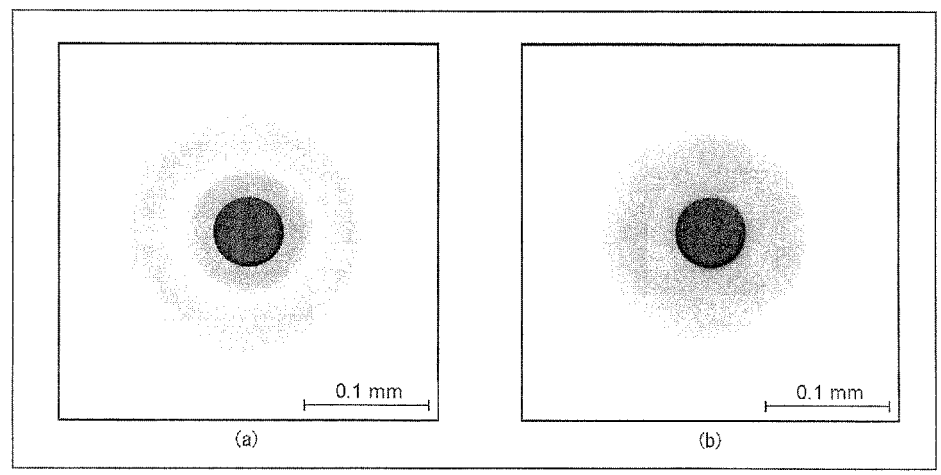
Figure 25:
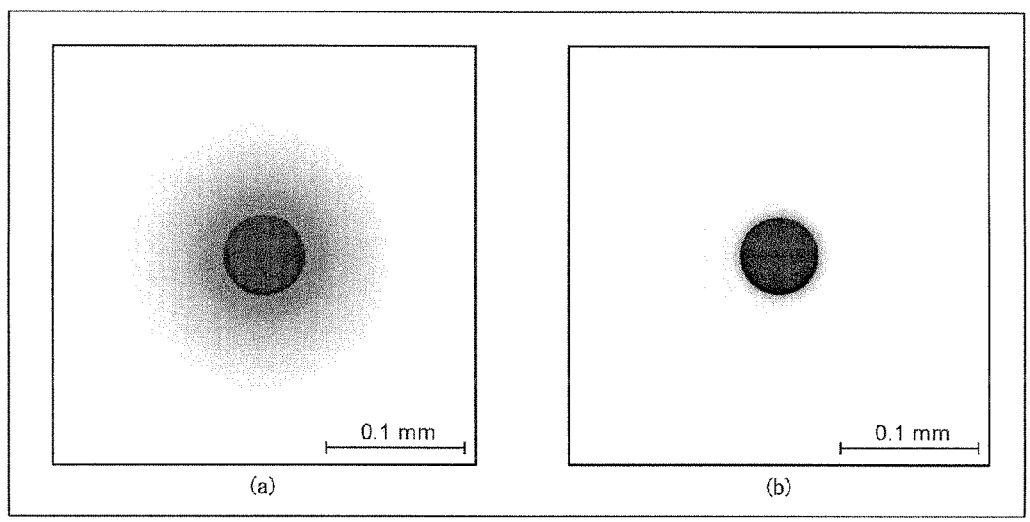

| Description of Signs and Numerals | |
|---|---|
| 10 | Intraocular lens (ophthalmic lens) |
| 13 | First far zone |
| 14 | Near zone |
| 15 | Second far zone |
| 30 | Intraocular lens (ophthalmic lens) |
| 32 | Near zone |
| 33 | Far zone |

The invention claimed is:

1. A multifocal ophthalmic lens, comprising:
a far zone for correcting a far vision; and
a near zone for correcting a near vision, arranged concentrically in an optical region of the lens; wherein
a power distribution is set to vary progressively in a radial direction of the far zone and the near zone,
power is altered discontinuously to have a stepwise power difference at a boundary between the far zone and the near zone,
a value of a power difference at the boundary between the far zone and the near zone is not greater than a maximum value of an intermediate power for correcting an intermediate vision, and
a mean power value in the near zone is less than an addition power prescribed for a patient as a proper power for correcting the near vision of the patient.

2. The multifocal ophthalmic lens in claim 1, wherein the ophthalmic lens includes an UV-absorber and/or a blue light blocking dye.

3. The multifocal ophthalmic lens in claim 1 is an intraocular lens to be implanted inside an eye.

4. The multifocal ophthalmic lens of claim 1, wherein a region having a mean power value that is negative relative to a reference power is included in the far zone.

5. The multifocal ophthalmic lens in claim 1, wherein a region of the far zone next to the near zone has the mean power value that is positive relative to a reference power.

6. The multifocal ophthalmic lens in claim 1, wherein a first far zone is arranged in a center zone of the optical region, and an annular near zone is arranged concentrically outside the first far zone, and an annular second far zone is arranged concentrically outside the annular near zone.

7. The multifocal ophthalmic lens in claim 1, wherein the near zone is arranged in a center zone of the optical region, and an annular far zone is arranged concentrically outside the region of the near zone.

8. A multifocal ophthalmic lens, comprising:
a far zone for correcting a far vision; and
a near zone for correcting a near vision, arranged concentrically in an optical region of the lens; wherein
a power distribution is set to vary progressively in a radial direction of the far zone and the near zone, power is altered discontinuously to have a stepwise power difference at a boundary between the far zone and the near zone, a value of a power difference at the boundary between the far zone and the near zone is not greater than a maximum value of an intermediate power for correcting an intermediate vision, and a region having a mean power value that is negative relative to a reference power is included in the far zone.

9. The multifocal ophthalmic lens in claim 8, wherein a region of the far zone next to the near zone has the mean power value that is positive relative to the reference power.

10. The multifocal ophthalmic lens in claim 8, wherein a first far zone is arranged in a center zone of the optical region, and an annular near zone is arranged concentrically outside the first far zone, and an annular second far zone is arranged concentrically outside the annular near zone.

11. The multifocal ophthalmic lens in claim 8, wherein the near zone is arranged in a center zone of the optical region, and an annular far zone is arranged concentrically outside the region of the near zone.

12. The multifocal ophthalmic lens in claim 8, wherein the ophthalmic lens includes an UV-absorber and/or a blue light blocking dye.

13. The multifocal ophthalmic lens in claim 8 is an intraocular lens to be implanted inside an eye.

14. A multifocal ophthalmic lens, comprising:
a far zone for correcting a far vision; and
a near zone for correcting a near vision, arranged concentrically in an optical region of the lens; wherein
a power distribution is set to vary progressively in a radial direction of the far zone and the near zone,
power is altered discontinuously to have a stepwise power difference at a boundary between the far zone and the near zone,
a value of a power difference at the boundary between the far zone and the near zone is not greater than a maximum value of an intermediate power for correcting an intermediate vision, and
a region of the far zone next to the near zone has the mean power value that is positive relative to a reference power.

15. The multifocal ophthalmic lens in claim 14, wherein a first far zone is arranged in a center zone of the optical region, and an annular near zone is arranged concentrically outside the first far zone, and an annular second far zone is arranged concentrically outside the annular near zone.

16. The multifocal ophthalmic lens in claim 14, wherein the near zone is arranged in a center zone of the optical region, and an annular far zone is arranged concentrically outside the region of the near zone.

17. The multifocal ophthalmic lens in claim 14, wherein the ophthalmic lens includes an UV-absorber and/or a blue light blocking dye.

18. The multifocal ophthalmic lens in claim 14 is an intraocular lens to be implanted inside an eye.

19. A multifocal ophthalmic lens, comprising:
a far zone for correcting a far vision; and
a near zone for correcting a near vision, arranged concentrically in an optical region of the lens; wherein
a power distribution is set to vary progressively in a radial direction of the far zone and the near zone,
power is altered discontinuously to have a stepwise power difference at a boundary between the far zone and the near zone,
a value of a power difference at the boundary between the far zone and the near zone is not greater than a maximum value of an intermediate power for correcting an intermediate vision,
a first far zone is arranged in a center zone of the optical region, and an annular near zone is arranged concentrically outside the first far zone, and an annular second far zone is arranged concentrically outside the annular near zone, and
the addition power value of a region of the near zone next to the second far zone is less than an addition power value of a region of the near zone next to the first far zone.

20. The multifocal ophthalmic lens of claim 19, wherein the power value of a region of the second far zone next to the near zone is less than the power value of a region of the first far zone next to the near zone.

21. The multifocal ophthalmic lens in claim 19, wherein the power value of an outer region of the second far zone is less than the power value of the region of the second far zone next to the near zone.

22. The multifocal ophthalmic lens in claim 19, wherein the mean power value of the outer region of the second far zone is negative relative to a reference power.

23. The multifocal ophthalmic lens in claim 19, wherein the ophthalmic lens includes an UV-absorber and/or a blue light blocking dye.

24. The multifocal ophthalmic lens in claim 19 is an intraocular lens to be implanted inside an eye.

25. A multifocal ophthalmic lens, comprising:
a far zone for correcting a far vision; and
a near zone for correcting a near vision, arranged concentrically in an optical region of the lens; wherein
a power distribution is set to vary progressively in a radial direction of the far zone and the near zone,
power is altered discontinuously to have a stepwise power difference at a boundary between the far zone and the near zone,
a value of a power difference at the boundary between the far zone and the near zone is not greater than a maximum value of an intermediate power for correcting an intermediate vision,
a first far zone is arranged in a center zone of the optical region, and an annular near zone is arranged concentrically outside the first far zone, and an annular second far zone is arranged concentrically outside the annular near zone, and
the power value of a region of the second far zone next to the near zone is less than the power value of a region of the first far zone next to the near zone.

26. The multifocal ophthalmic lens in claim 25, wherein the power value of an outer region of the second far zone is less than the power value of the region of the second far zone next to the near zone.

27. The multifocal ophthalmic lens in claim 25, wherein the mean power value of the outer region of the second far zone is negative relative to a reference power.

28. The multifocal ophthalmic lens in claim 25, wherein the ophthalmic lens includes an UV-absorber and/or a blue light blocking dye.

29. The multifocal ophthalmic lens in claim 25 is an intraocular lens to be implanted inside an eye.

30. A multifocal ophthalmic lens, comprising:
a far zone for correcting a far vision; and
a near zone for correcting a near vision, arranged concentrically in an optical region of the lens; wherein a power distribution is set to vary progressively in a radial direction of the far zone and the near zone, power is altered discontinuously to have a stepwise power difference at a boundary between the far zone and the near zone, a value of a power difference at the boundary between the far zone and the near zone is not greater than a maximum value of an intermediate power for correcting an intermediate vision, a first far zone is arranged in a center zone of the optical region, and an annular near zone is arranged concentrically outside the first far zone, and an annular second far zone is arranged concentrically outside the annular near zone, and the power value of an outer region of the second far zone is less than the power value of the region of the second far zone next to the near zone.

31. The multifocal ophthalmic lens in claim 30, wherein the mean power value of the outer region of the second far zone is negative relative to a reference power.

32. The multifocal ophthalmic lens in claim 30, wherein the ophthalmic lens includes an UV-absorber and/or a blue light blocking dye.

33. The multifocal ophthalmic lens in claim 30 is an intraocular lens to be implanted inside an eye.

34. A multifocal ophthalmic lens, comprising:
a far zone for correcting a far vision; and
a near zone for correcting a near vision, arranged concentrically in an optical region of the lens; wherein
a power distribution is set to vary progressively in a radial direction of the far zone and the near zone,
power is altered discontinuously to have a stepwise power difference at a boundary between the far zone and the near zone,
a value of a power difference at the boundary between the far zone and the near zone is not greater than a maximum value of an intermediate power for correcting an intermediate vision,
a first far zone is arranged in a center zone of the optical region, and an annular near zone is arranged concentrically outside the first far zone, and an annular second far zone is arranged concentrically outside the annular near zone, and
the mean power value of the outer region of the second far zone is negative relative to a reference power.

35. The multifocal ophthalmic lens in claim 34, wherein the ophthalmic lens includes an UV-absorber and/or a blue light blocking dye.

36. The multifocal ophthalmic lens in claim 34 is an intraocular lens to be implanted inside an eye.

37. A multifocal ophthalmic lens, comprising:
a far zone for correcting a far vision; and
a near zone for correcting a near vision, arranged concentrically in an optical region of the lens; wherein
a power distribution is set to vary progressively in a radial direction of the far zone and the near zone,
power is altered discontinuously to have a stepwise power difference at a boundary between the far zone and the near zone,
a value of a power difference at the boundary between the far zone and the near zone is not greater than a maximum value of an intermediate power for correcting an intermediate vision,
the near zone is arranged in a center zone of the optical region, and an annular far zone is arranged concentrically outside the region of the near zone, and the mean power value of the outer region of the far zone is negative relative to a reference power.

38. The multifocal ophthalmic lens in claim 27, wherein the ophthalmic lens includes an UV-absorber and/or a blue light blocking dye.

39. The multifocal ophthalmic lens in claim 27 is an intraocular lens to be implanted inside an eye.

40. A multifocal ophthalmic lens, comprising:
at least one far zone for correcting a far vision;
at least one near zone for correcting a near vision, arranged concentrically in an optical region of the lens,
wherein a power distribution is set to vary progressively in radial direction of the far zone and the near zone;
power is altered discontinuously to have a stepwise power difference at a boundary between the far zone and the near zone;
a progressive power distribution of the near zone in the vicinity of the boundary between the far zone and the near zone, has a value close to a maximum value of an intermediate power for correcting an intermediate vision at the boundary;
the progressive power distribution of the near zone is designed to have a mountain-shaped power distribution, and the maximum value at a peak of this mountain-shaped power distribution is set to a power required for correcting visual acuity for seeing an object at the intended nearest distance or at a reading distance;
the progressive power distribution of the near zone is a distribution in which power gradually increases from the boundary between the near zone an the far zone to the peak of the mountain-shaped power distribution; and
the mean power value of the far zone is less than a reference power.

41. The multifocal ophthalmic lens in claim 40, wherein the ophthalmic lens includes an UV-absorber and/or a blue light blocking dye.

42. The multifocal ophthalmic lens in claim 40 is an intraocular lens to be implanted inside an eye.

43. A multifocal ophthalmic lens, comprising:
a far zone for correcting a far vision; and
a near zone for correcting a near vision, arranged concentrically in an optical region of the lens; wherein
a power distribution is set to vary progressively in a radial direction of the far zone and the near zone,
power is altered discontinuously to have a stepwise power difference at a boundary between the far zone and the near zone,
a value of a power difference at the boundary between the far zone and the near zone is not greater than a maximum value of an intermediate power for correcting an intermediate vision,
the near zone is arranged in a center zone of the optical region, and an annular far zone is arranged concentrically outside the region of the near zone,
the power value of the outer region of the far zone is less than the power value of the region of the far zone next to the near zone, and
the mean power value of the outer region of the far zone is negative relative to a reference power.

44. The multifocal ophthalmic lens in claim 43, wherein the ophthalmic lens includes an UV-absorber and/or a blue light blocking dye.

45. The multifocal ophthalmic lens in claim 43 is an intraocular lens to be implanted inside an eye.

* * * * *